United States Patent
Maher et al.

(10) Patent No.: US 11,040,124 B2
(45) Date of Patent: Jun. 22, 2021

(54) METHOD OF AND A MOLD FOR THE MANUFACTURE, MAKING AND/OR PRODUCTION OF A MULTI-COMPONENT IMPLANT, DEVICE, CONSTRUCT OR MATERIAL

(71) Applicant: NEW YORK SOCIETY FOR THE RUPTURED AND CRIPPLED MAINTAINING THE HOSPITAL FOR SPECIAL SURGERY, New York, NY (US)

(72) Inventors: Suzanne A. Maher, Highland Lakes, NJ (US); Tony Chen, Highland Park, NJ (US); Russell Warren, Greenwich, CT (US)

(73) Assignee: NEW YORK SOCIETY FOR THE RUPTURED AND CRIPPLED MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 0 days.

(21) Appl. No.: 16/498,211

(22) PCT Filed: May 1, 2018

(86) PCT No.: PCT/US2018/030377
§ 371 (c)(1),
(2) Date: Sep. 26, 2019

(87) PCT Pub. No.: WO2018/204315
PCT Pub. Date: Nov. 8, 2018

(65) Prior Publication Data
US 2020/0376168 A1 Dec. 3, 2020

Related U.S. Application Data

(60) Provisional application No. 62/492,535, filed on May 1, 2017.

(51) Int. Cl.
*B29C 45/03* (2006.01)
*A61L 27/52* (2006.01)
(Continued)

(52) U.S. Cl.
CPC .............. *A61L 27/52* (2013.01); *A61L 27/16* (2013.01); *A61L 27/56* (2013.01); *A61L 27/58* (2013.01);
(Continued)

(58) Field of Classification Search
CPC ..... B29C 45/0053; B29C 45/03; B29C 45/14; B29C 45/16; B29C 45/26; B29C 45/7207;
(Continued)

(56) References Cited

U.S. PATENT DOCUMENTS 8,475,503 B2 7/2013 Denoziere et al.
2006/0178748 A1 8/2006 Dinger, III et al.
(Continued)

OTHER PUBLICATIONS

Bekkers et al., (Nov. 24, 2009). "Treatment selection in articular cartilage lesions of the knee: a systematic review." Am. J. Sports Med. 37 Suppl 1: 148S-155S.
(Continued)

*Primary Examiner* — Jeffrey M Wollschlager
*Assistant Examiner* — Xue H Liu
(74) *Attorney, Agent, or Firm* — Leason Ellis LLP

(57) ABSTRACT

An improved new method of making a multi-component implant comprising a solid hydrogel, a porous hydrogel, and a porous rigid base suitable for implantation into a mammal, to treat, repair or replace defects and/or injury biological tissue as well as the implant made from the improved method. The invention also includes an improved method for making devices, constructs, and materials comprising a hydrogel and a porous rigid material. The invention also includes a mold and kits for performing the methods.

12 Claims, 13 Drawing Sheets

(51) Int. Cl.
| | |
|---|---|
| *A61L 27/16* | (2006.01) |
| *A61L 27/56* | (2006.01) |
| *A61L 27/58* | (2006.01) |
| *B29C 45/00* | (2006.01) |
| *B29C 45/14* | (2006.01) |
| *B29C 45/16* | (2006.01) |
| *B29C 45/26* | (2006.01) |
| *B29C 45/72* | (2006.01) |
| *B29K 29/00* | (2006.01) |
| *B29K 105/00* | (2006.01) |
| *B29K 105/04* | (2006.01) |

(52) U.S. Cl.
CPC .......... *B29C 45/0053* (2013.01); *B29C 45/03* (2013.01); *B29C 45/14* (2013.01); *B29C 45/16* (2013.01); *B29C 45/26* (2013.01); *B29C 45/7207* (2013.01); *A61L 2400/06* (2013.01); *A61L 2400/08* (2013.01); *A61L 2430/02* (2013.01); *A61L 2430/06* (2013.01); *B29C 2045/1693* (2013.01); *B29K 2029/04* (2013.01); *B29K 2105/0061* (2013.01); *B29K 2105/04* (2013.01); *B29K 2239/06* (2013.01)

(58) Field of Classification Search
CPC ........ B29C 2045/1693; B29K 2029/04; B29K 2105/0061; B29K 2105/04; B29K 2239/06
See application file for complete search history.

(56) References Cited

U.S. PATENT DOCUMENTS

| | | |
|---|---|---|
| 2007/0179621 A1 | 8/2007 | Mcclellan, III et al. |
| 2007/0179622 A1 | 8/2007 | Denoziere et al. |
| 2009/0017096 A1 | 1/2009 | Lowman et al. |
| 2011/0288199 A1 | 11/2011 | Lowman et al. |
| 2012/0178836 A1 | 7/2012 | Maher et al. |
| 2014/0324169 A1 | 10/2014 | Maher et al. |
| 2016/0287392 A1 | 10/2016 | Patrick et al. |
| 2017/0209624 A1 | 7/2017 | Maher et al. |

OTHER PUBLICATIONS

Choi et al., (Apr. 20, 1990) "The elastic moduli of human subchondral, trabecular, and cortical bone tissue and the size-dependency of cortical bone modulus." Journal of Biomechamics 23(11):1103-13.

Cole and Lee, (Dec. 2003) "Complex knee reconstruction: articular cartilage treatment options." Arthroscopy 19 Suppl 1: 1-10.

Deneweth et al., (2013) "Heterogeneity of tibial plateau cartilage in response to a physiological compressive strain rate." J. Orthop. Res. 31(3):370-5.

Gilbert et al., (2013) "Dynamic contact mechanics on the tibial plateau of the human knee during activities of daily living." Journal of Biomechanics 47(9):2006-12. Jun. 27, 2014.

Guo et al., (Jun. 1, 2015) "A statistically-augmented computational platform for evaluating meniscal function." Journal of Biomechanics 48(8):1444-53.

Magnussen et al., (Jan. 12, 2008) "Treatment of focal articular cartilage defects in the knee: a systematic review." Clin. Orthop. Relat. Res. 466(4): 952-962.

Maher et al., (Mar. 27, 2007) "Nondegradable hydrogels for the treatment of focal cartilage defects." Journal of Biomedical Materials Research Part A 83(1):145-55.

Mauck et al. (Aug. 14, 2002). "Influence of seeding density and dynamic deformational loading on the developing structure/function relationships of chondrocyte-seeded agarose hydrogels." Ann. Biomed. Eng. 30(8):1046-1056.

Radin et al., (Apr. 1970) "A comparison of the dynamic force transmitting properties of subchondral bone and articular cartilage." J. Bone Joint Surg. Am. 52(3):444-56.

Shelbourne et al., (Jan. 2003). "Outcome of untreated traumatic articular cartilage defects of the knee: a natural history study." J. Bone Joint Surg. Am. 85-A Suppl 2:8-16.

Woodfield, (2000) "Interfacial Shear Strength Criteria for Tissue-Engineered Cartilage Anchored to Porous Synthetic Scaffolds" Masters Thesis, University of Toronto. Reference is believed to predate application priority date.

Ng, Kenneth W. et al. (May 11, 2012) "A Novel Macroporous Polyvinyl Alcohol Scaffold Promotes Chondrocyte Migration and Interface Formation in an In Vitro Cartilage Defect Model", Tissue Engineering, vol. 18, Nos. 11 and 12.

4-Hole

1-Hole

Dovetail

METHOD OF AND A MOLD FOR THE MANUFACTURE, MAKING AND/OR PRODUCTION OF A MULTI-COMPONENT IMPLANT, DEVICE, CONSTRUCT OR MATERIAL

CROSS-REFERENCE TO RELATED PATENT APPLICATIONS

The present application is a U.S. National Phase Application under 35 U.S.C. § 371 of International Patent Application No. PCT/US2018/030377, filed May 1, 2018, and claims priority to U.S. Patent Application Ser. No. 62/492,535, filed May 1, 2017, which is hereby incorporated by reference in its entirety. The International Application was published on Nov. 8, 2018, as International Publication No. WO 2018/204315 A1.

This invention was made with Government support under AR067533 awarded by the NIH. The Government has certain rights in the invention.

FIELD OF THE INVENTION

The present invention relates to an improved method of making, manufacturing and/or producing a multi-component implant comprising a solid hydrogel, a porous hydrogel, and a porous rigid base suitable for implantation into a mammal. The present invention also provides for a method of making, manufacturing and/or producing a device, construct or material comprising a solid hydrogel or other polymer and a porous rigid material. The present invention also includes a mold for carrying out the methods of the invention.

BACKGROUND OF THE INVENTION

Articular cartilage defects in joints are a significant source of pain, have a limited ability to heal and can lead to the development of osteoarthritis (Shelbourne et al., 2003). Surgical options for symptomatic cartilage defects include palliative, reparative, and restorative methods (Cole and Lee, 2003). The treatment algorithm and surgical indications for each of these procedures continues to evolve (Magnussen et al., 2008; Bekkers et al., 2009). Alternative treatments have been developed using biodegradable implants intended to encourage the formation of articular cartilage within the defect site. However, these implants have mechanical properties that are continually changing and often inferior to that of the native tissue during the regeneration process (Mauck et al., 2002). Furthermore, these implants rely on a controlled and robust cellular response in order to recreate an organized tissue that looks and mechanically functions like the native articular cartilage, a goal that has thus far proven elusive in the biological environment of the defective joint.

Another method to treat this clinical problem is to use well characterized, non-biodegradable implants capable of resisting in vivo mechanical loads immediately after implantation and for the duration of the regeneration process. Non-degradable constructs should ideally: (i) integrate with adjacent tissue; (ii) transmit loads much in the way of the native tissue that the implant is intended to replace; (iii) transfer load to the underlying bone (to avoid bony resorption); (iv) resist wear; (v) not cause abrasion to opposing cartilage surfaces; and (vi) allow for easy implantation and fixation to the surrounding tissues.

A multicomponent implant disclosed and claimed in co-owned U.S. Pat. No. 9,543,310 solves these problems and provides for a novel multi-component implant for the treatment, repair or replacement of defects and injuries in biological tissue, especially musculoskeletal tissue.

However, a reliable method of making such an implant was needed as the previous method resulted in implant failure at the interface of the two dissimilar components, the solid hydrogel and the porous rigid base.

Additionally, several biomedical devices, constructs and materials are made from a hydrogel and a porous rigid material. These devices, constructs and materials can also fail at the interface of these two very dissimilar materials.

Thus, there is a need in the art for a method of making implants, devices, constructs and materials comprising hydrogels and porous rigid materials that withstand forces and do not fail at the interface.

SUMMARY OF THE INVENTION

The present invention overcomes the problems in the art by providing a novel method for making, manufacturing and/or producing a multicomponent implant for treating, repairing, and/or replacing a defect and/or injury in biological tissue, more specifically musculoskeletal tissue, that meets the six requirements set forth above.

The present invention also provides for a novel method of making, manufacturing and/or producing a device, construct, or material comprising a hydrogel and a porous rigid material with an interface that maximizes integration between the two very different layers, the hydrogel and the porous rigid material. The present invention also includes the device, construct, or material made from the method of the invention.

The present invention also provides for a novel method of making, manufacturing and/or producing a device, construct, or material comprising an elastic polymer and a porous rigid material with an interface that maximizes integration between the two very different layers, the elastic polymer and the porous rigid material. The present invention also includes the device, construct, or material made from the method of the invention.

Such a devices, constructs or materials have biomedical applications including drug delivery devices, biosensor devices, augmenting tissue function, and treating disease and injury. These devices, constructs, and materials can also be used for other applications such as use in automotive and aircraft and aerospace technologies.

Thus one embodiment of the present invention is a method of making, manufacturing and/or producing an implant suitable for implantation into a mammal for the treatment, repair or replacement of defects or injury in biological tissue, comprising:
a. placing a porous rigid base into a well in a base of a mold;
b. placing a porous hydrogel in the well on top of the porous rigid base;
c. placing a first lid on the mold;
d. introducing or injecting a first low viscosity polymer into the well in the base of the mold;
e. freezing the mold to about −20° C. for about 4 to 24 hours and subsequently thawing the mold at about 23° C. for about 4 to 12 hours;
f. removing the first lid and removing excess low viscosity polymer;
g. placing a second lid on the mold;
h. introducing or injecting a second low viscosity polymer into the well in the base of the mold;

i. freezing the mold to about −20° C. for about 4 to 24 hours and subsequently thawing the mold at about 23° C. for about 4 to 12 hours;
j. removing the second lid;
k. placing a third lid on the mold, said third lid capable of defining the curvature of the surface of the implant;
l. displacing the porous rigid base for a defined distance;
m. freezing the mold to about −20° C. for about 4 to 24 hours and subsequently thawing the mold at about 23° C. for about 4 to 12 hours, for about six to about twelve times, to obtain the implant comprising the porous rigid base, with a solid hydrogel surrounded by the porous hydrogel.

In some embodiments, the porous hydrogel is manufactured comprising the steps:
a. soaking a degradable polymer sponge in a non-biodegradable polymer in a solvent;
b. freezing the sponge to about −20° C. for about 4 to 24 hours and subsequently thawing the sponge at about 23° C. for about 4 to 12 hours; and
c. removing a center section from the sponge after performing steps a. and b.

The result of the method of the invention is a novel implant comprising at least three components: a solid hydrogel or polymer; a porous hydrogel or polymer that can surround the solid hydrogel or polymer; and a porous rigid base. The solid hydrogel and porous rigid base resist joint load, and the porous hydrogel and the porous rigid base allow for cellular migration into and around the implant. The resulting implant of the present invention can also comprise an interface that maximizes integration between the two very different layers—the hydrogel and the porous rigid base.

A further embodiment of the present invention is a multicomponent implant made, manufactured and/or produced by the method set forth herein.

The method of the current invention results in the multicomponent implant described and claimed in co-owned U.S. Pat. No. 9,545,310, hereinafter incorporated by reference in its entirety (hereinafter the '310 patent).

A further embodiment of the present invention is a method of making, manufacturing and/or producing a device, construct, or material comprising a hydrogel and a porous rigid material, comprising:
a. placing a porous rigid material into a well in a carrier;
b. introducing or injecting a first low viscosity polymer into the carrier;
c. freezing the carrier to about −20° C. for about 4 to 24 hours and subsequently thawing the carrier at about 23° C. for about 4 to 12 hours;
d. introducing or injecting a second low viscosity polymer into the carrier;
e. freezing the carrier to about −20° C. for about 4 to 24 hours and subsequently thawing the carrier at about 23° C. for about 4 to 12 hours; and
f. freezing the carrier to about −20° C. for about 4 to 24 hours and subsequently thawing the carrier at about 23° C. for about 4 to 12 hours about 6 to 12 times.

The result of this method of the invention is a novel device, construct, or material comprising a hydrogel and a porous rigid material with an interface that maximizes integration between the two very different layers, thus resisting failure.

Yet a further embodiment of the present invention is a method of making, manufacturing and/or producing a device, construct, or material comprising an elastic polymer and a porous rigid material with an interface, comprising:
a. placing a porous rigid material into a carrier;
b. introducing or injecting a first low viscosity polymer into the carrier, said carrier containing a chemical crosslinking agent;
c. incubating the first low viscosity polymer with the chemical crosslinking agent for a time and at a temperature to allow the chemical crosslinking agent to partially crosslink the first polymer to create an interface layer;
d. introducing or injecting a second low viscosity polymer into the carrier, said carrier containing a chemical crosslinking agent;
e. incubating the second low viscosity polymer with the chemical crosslinking agent for a time and at a temperature to allow the chemical crosslinking agent to crosslink the second polymer until the desired crosslinking percentage is reached and a layered elastic polymer is created; and
f. washing the elastic polymer to remove unreacted crosslinker and polymer.

The result of this method of the invention is a novel device, construct, or material comprising an elastic polymer and a porous rigid material with an interface that maximizes integration between the two very different layers, thus resisting failure.

The present invention also provides for molds, carriers, and kits for performing the methods of the invention.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

FIG. 11A shows the mold with the first lid. FIG. 11B shows the mold with the second lid. FIG. 11C shows the mold with the third lid.

DETAILED DESCRIPTION OF INVENTION

Definitions

Figure 1:
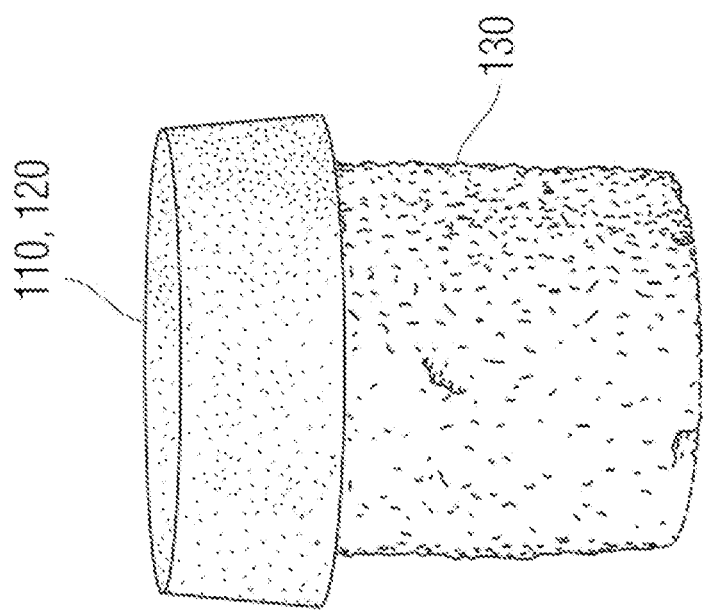
FIG. 1 is a side perspective view of one exemplary implant made by the method of the invention.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The terms "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The terms "implant", "device", and "construct", are used interchangeably throughout this application and can mean any material inserted or grafted into the body. Biomedical uses of such implants, devices and constructs include but are not limited to drug delivery, biosensoring, repair and/or replacement of tissue, treating disease, defect and/or injury, and augmenting tissue function. Devices, constructs and materials may have applications outside of the biomedical field.

The term "porous" as used in the application means having pores, which are defined as a minute opening.

The term "micropores" as used in the application means pores with a diameter of less than about 1 mm, and the term "microporous" means having micropores or pores with a diameter less than about 1 mm.

The term "macropores" as used in the application means pores with a diameter greater than about 1 mm, and the term "macroporous" means having macropores or pores with a diameter greater than about 1 mm.

The term "interconnected" as used in the application means having internal connections or continuity between parts or elements.

The term "rigid" as used in the application means a porous material that has an elastic modulus that is about at least 20 times greater than the hydrogel or polymer with which it is interfaced. This minimum fold difference was determined from the previously measured elastic moduli for cartilage (ranges from 7.01 MPa to 40 MPa) (Deneweth et al., 2012; Radin et al., 1970) and bone (785 to 1,115 MPa) (Radin et al., 1970; Choi et al., 1990). In some embodiments, the porous rigid base can have an elastic modulus greater than bone.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The terms "treat", "treatment", and the like refer to a means to slow down, relieve, ameliorate or alleviate at least one of the symptoms of the defect or injury or reverse the defect or injury after its onset.

The term "repair" and the like refer to any correction, reinforcement, reconditioning, remedy, making up for, making sound, renewal, mending, patching, or the like that restores function. Accordingly, the term "repair" can also mean to correct, to reinforce, to recondition, to remedy, to make up for, to make sound, to renew, to mend, to patch or to otherwise restore function.

The term "replace", "replacement", and the like refer to a means to substitute or take the place of. In some embodiments, the term means to substitute or take the place of defective or injured tissue.

The term "defect" and the like refer to a flaw or a physical problem in a structure, or system, especially one that prevents it from functioning correctly, or a medical abnormality Defects can include, but are not limited to, wounds, ulcers, burns, natural defects, such as birth defects, and any other defects of biological tissue, including skin, bone, cartilage, muscle, tendon, ligament, meniscus, temporomandibular joint, arteries and blood vessels, and organs.

The term "injury" and the like refer to wound or trauma; harm or hurt; usually applied to damage inflicted on the body by an external force.

The term "biological tissue" as used herein includes but is not limited to musculoskeletal, including bone, tendon, ligaments, cartilage and the discs of the spine; vascular, including but not limited to, arteries, vessels, and heart valves; epidermal and dermal; connective tissue, including but not limited to, subcutaneous tissue; neurological and the associated dura tissue surrounding the brain and spinal cord; and dental.

The term "polymer" means a large molecule composed of repeating structural units often connected by covalent chemical bonds. Polymers can be natural or synthetic. "Biodegradable polymers" are those that can be degraded by living organisms or molecules produced by living organisms such as enzymes and other proteins, and "non-biodegradable polymers" cannot be degraded by such enzymes or proteins. The non-biodegradable polymer as used herein means any polymer that has mechanical properties that can be controlled separately by varying the polymer concentration and/or the method of polymerization such as freeze/thawing.

"Degradable polymers" include biodegradable polymers as well as polymers that can be degraded using other methods such as but not limited to acid/base erosion, solubilization and melting.

"Non-degradable polymers" cannot be degraded by anything.

The term "hydrogel" means a degradable or non-degradable natural or synthetic polymer network which is hydrophilic and can absorb a high amount of water. The hydrogel as used herein means any hydrogel that has mechanical properties that can be controlled separately by varying the polymer and water concentrations and/or the method of gelation such as freeze/thawing.

The terms "polymerization" and "gelation" and the like refer to a means to polymerize, solidify, gel, interconnect, integrate, and the like to form polymer or hydrogel three-dimensional networks.

The term "biocompatible" as used in the application means capable of coexistence with living tissues or organisms without causing harm.

The term "agent" as used herein means a substance that produces or is capable of producing an effect and would include, but is not limited to, chemicals, pharmaceuticals, biologics, small organic molecules, cells, blood products, antibodies, nucleic acids, peptides, and proteins.

The term "supplemental agent" as used herein would mean an agent that is added to the implant to impart beneficial properties to the implant.

The Multi-Component Implant

A novel multi-component implant as set forth in the '301 patent and shown in FIG. 1, comprises a solid hydrogel 110 to resist load, a porous hydrogel layer 120 to enable cellular infiltration and implant-tissue integration, and a porous rigid base 130 to which the solid and porous hydrogels 110, 120 are both attached.

There are many advantages to the implant made by the present invention. Integration between the implant, and cartilage and bone tissue simultaneously occur. Loads acting on the hydrogel surface are transmitted through the hydrogel solid 110 to the porous rigid base 130 and underlying bone.

Methods of Manufacture of a Multi-Component Implant

The objective of the current invention was to modify the hydrogel-porous rigid base, e.g., PVA-metal, interface to prevent mechanical failures of the device in a repetitively loaded joint. To start, the strength of the hydrogel-porous rigid base interface was optimized to withstand physiological stresses by changing the macroscopic geometry of the interface, and the stiffness of the hydrogel at the hydrogel-porous rigid base interface. The effect of different design features on interface shear and tensile stresses during simulated walking combinations were assessed in previously developed finite element (FE) models of human knees. Designs that maintained surface contact stresses within 10% of the intact knee and had the highest safety factors (i.e., failure stress as measured experimentally, divided by the maximum interfacial stress computed in the FE model), were then manufactured and physically tested under cyclic loading conditions.

The current method of the invention improved on the previous method in many ways. First it was determined that higher concentration PVA hydrogels could be created using dimethyl sulfoxide (DMSO) as the solvent while maintaining the same mechanical properties (Examples 1-3). Hydrogels of different concentrations could be layered and create a gradual transition between the two zones (Example 4).

Additionally, the porous rigid base with a single macroporous hole was identified as the optimal design (Example 8).

Lastly, the new method of assembling the implant in a mold of the invention, resulted in an implant that can better withstand joint loads. The interfacial strength of the implant was vastly improved by creating a layered hydrogel with a gradual transition between the top load bearing region or layer (e.g., 20% PVA) to the interface region or layer (e.g., 35% PVA). The unique method of manufacture described herein allows for creation of a consistent interface layer (Examples 7-10).

To obtain the implant meeting the criteria set forth above, the method of manufacture can comprise the following steps:

a. placing a porous rigid base 130 into a well 220 in a base 210 of a mold 200;
b. placing a porous hydrogel 120 in the well 220 in the base 210 of the mold 200 on top of the porous rigid base 130 and along the wall of the well 220;
c. placing a first lid 230 on the base 210 of the mold 200;
d. introducing or injecting a first low viscosity polymer into the well 220 of the mold 200 using a tool 310;
e. freezing the mold 200 with the first lid 230 containing with the porous rigid base 130 and the porous hydrogel 120 and the injected low viscosity polymer, to about −20° C. for about 4 to 24 hours and subsequently thawing the mold 200 at about 23° C. for about 4 to 12 hours;
f. removing the first lid 230;
g. placing a second lid 240 on the base 210 of the mold 200, wherein the well 220 of the mold 200 contains a porous rigid base 130, an interface layer of a solid hydrogel 140, and a porous hydrogel 120;
h. introducing or injecting a second low viscosity polymer into the well 220 of the mold 200 with tool 310;
i. freezing the mold 200 to about −20° C. for about 4 to 24 hours and subsequently thawing the mold 200 at about 23° C. for about 4 to 12 hours;
j. removing the second lid 240;
k. placing a third lid 250 on the base 210 of the mold 200, wherein the well 220 of the mold 200 contains a porous rigid base 130, an interface layer of a solid hydrogel 140, a porous hydrogel 120, and a load bearing layer of a solid hydrogel 110, and wherein the third lid 250 has a curvature ranging from about 0 mm to about 2 mm;
l. displacing the porous rigid base 130 with a tool 320 that displaces the porous rigid base a distance defined by the desired final curvature of the implant;
m. freezing the mold 200 with the third lid 250, wherein the well 220 of the mold 200 contains the porous rigid base 130, the porous hydrogel 120, an interface layer of a solid hydrogel 140, and a load bearing layer of a solid hydrogel 110 to about −20° C. for about 4 to 24 hours and subsequently thawing the mold 200 at about 23° C. for about 4 to 12 hours, for about six to about twelve times;
n. removing the third lid 250, to obtain an implant comprising a porous rigid base 130, a porous hydrogel 120, an interface layer of a solid hydrogel 140, and a load bearing layer of a solid hydrogel 110; and
o. removing any biodegradable polymer from the porous hydrogel 120.

Preparation of the Porous Rigid Base

The porous rigid base can be manufactured to contain many different features, including but not limited to, a step at the hydrogel-base interface and macroporous structures to improve mechanical interlock between the two layers, and a taper on the bottom of the porous rigid base to allow alignment of the device with the defect.

Preferred materials for the porous rigid base include but is not limited to, bone, metal such as titanium, polyetherketoneketone (PEKK), polyetheretherketone (PEEK), and bioactive glass (e.g., silicone oxide, sodium oxide). This porous rigid base can contain micropores ranging from about 150 to 500 µm in size.

The porous rigid base can comprise geometric features, such as holes, macropores, and steps.

Macropores, i.e., holes, ranging from about 1% to 90% of the porous rigid base in diameter and from about 10% to 50% of the porous rigid base depth are created in the surface of the porous rigid base, which contains micropores, to further increase interdigitation between the hydrogel and the porous rigid base.

A preferred embodiment of the implant is a porous rigid base with a single macropore or hole. See FIGS. 8A-8C.

Preparation of the Porous Hydrogel Portion

The general method for making the porous hydrogel portion of the implant requires:
 a. soaking a degradable polymer sponge in a non-biodegradable polymer in a solvent;
 b. freezing the sponge to about −20° C. for about 4 to 24 hours and subsequently thawing the sponge at about 23° C. for about 4 to 12 hours; and
 c. removing a center section from the sponge after performing steps a. and b.

The hydrogel portion of the implant is preferably prepared using an interconnected sponge which is made of or contains a biodegradable polymer.

The sponge can also be made of or contain biodegradable polymers including, but not limited to, gelatin, collagen, poly(lactic acid), poly(glycolic acid), chitosan, and alginate or degradable substance such as salts and polyethylene glycol.

Moreover the sponge's size, porosity and wall thickness can be varied depending on the needs of the final implant.

The sponge is hydrated by soaking it in deionized water for 1 hour to 5 days, with about 12 hours being preferred. A person of skill in the art would easily be able to determine a sufficient amount of time wherein the sponge is saturated with water.

The sponge is then centrifuged to remove the trapped air bubbles. The preferred method is at 3000 g for 1 hour at a time, 3-5 times, with gentle agitation between the centrifugations to restore the original shape. However, a person of skill could easily determine the extent of centrifugation necessary to remove air bubbles from the sponge. Another technique is the intermittent application of a vacuum for 30 minutes on and 30 minutes off, with agitation between the vacuum steps, for 3-5 times.

The next step in the method of the invention is replacement of the water in the sponge with a non-biodegradable polymer in a solvent. A preferred solvent is dimethyl sulfoxide (DMSO).

While poly(vinyl) alcohol or PVA is preferred, any non-biodegradable polymer which has mechanical properties that can be controlled separately by varying the polymer concentration and/or the method of polymerization such as freeze/thawing can be used. Examples of other non-biodegradable polymers that can be used are polyvinyl pyrrolidone, polyacrylamide, polyethylene glycol, polyurethane, and combinations thereof.

The mechanical properties of the final device are determined by the final concentration of the polymer, e.g., PVA, in the device. Generally, the higher the final concentration of polymer in the device, the stiffer the device. A device with a higher concentration of polymer can generally withstand a higher load.

As shown in Example 3, it was surprisingly found that increased amounts of PVA can be used when DMSO is the solvent while maintaining the same mechanical properties.

The polymer is substituted into the sponge under gentle agitation in steps of increasing concentration up to the desired concentration. Polymer solutions of varying concentration are made and the sponges soaked until the desired concentration is obtained. The polymer solutions range from 1% to 40% weight/volume solutions, up to the desired final concentration, with the preferred final concentration of polymer ranging from 10% to 40%. The preferred final concentration will depend upon the final use of the implant, as determined by the person of skill. The preferred final concentration of polymer is 10%.

The polymer, e.g., PVA, hydrogels are then subject to a series of freeze/thaw cycles. PVA offers the advantage of being physically cross-linked using freeze/thaw cycles, without the need for use of potentially toxic cross-linking agents. During freezing, the solvent (water or DMSO for PVA) freezes and cause regions of high PVA cross-links to form. As the PVA chains come in close contact with one another, crystallite formation and hydrogen bonding can occur between the chains. These interactions remain intact following thawing, and thereby create a three-dimensional network. Thus, the mechanical properties of the hydrogel can be controlled by increasing the number of freeze/thaw cycles such that the amount of hydrogen bonding and crystallite formation can be increased. The increase in freeze/thaw cycles increases the strength of the construct. The mechanical properties can also be controlled by the duration and rate of freezing and thawing. The preferred method involves freezing the sponge at about −20° C. for about 4 to about 24 hours, with 20 hours being preferred and then thawing the construct at about 23° C. for about 4 to about 12 hours, with 4 hours being preferred. However, this part of the process can be easily varied by the person of skill in order to vary the mechanical properties of the construct as desired. Both the number of hours of freezing and/or thawing can be varied as well as the number of cycles. When PVA in DMSO is used, the preferred number of freeze/thaw cycles ranges from about eight to eleven, with eight being preferred.

After the freeze/thaw cycle, the center of the sponge is cored in order to form a porous hydrogel. One of skill in the art can determine the size of the outer diameter of the final porous hydrogel which generally can range from about 10 mm to about 25 mm.

Preparation of Layered Solid Hydrogel

The improved method of manufacture of the invention includes the preparation of a solid hydrogel that is layered, meaning the solid hydrogel is composed of non-degradable polymers in different concentrations, in different zones of the hydrogel. In a preferred embodiment, there is a gradual transition between the layers of different concentrations of polymer. In one embodiment, there are two layers comprising different concentrations of non-degradable polymer, in the solid hydrogel. In some embodiments, there are more than two layers in the solid hydrogel.

In some embodiments, the polymer is in a solvent. The preferred solvent is DMSO.

Figure 8A:
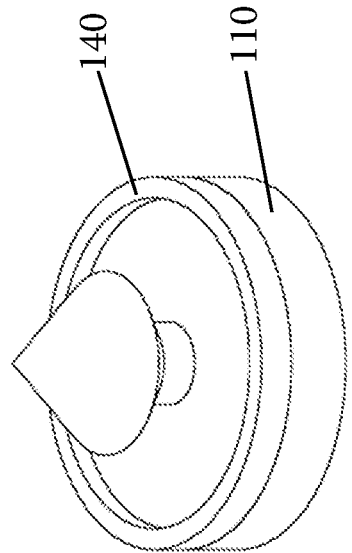
FIGS. 8A-8C show the models of the three different implant configurations made of a 20% PVA layer, and a 35% PVA layer and having the tail structure that fills the macroporous features of the metal base.
Figure 8B:
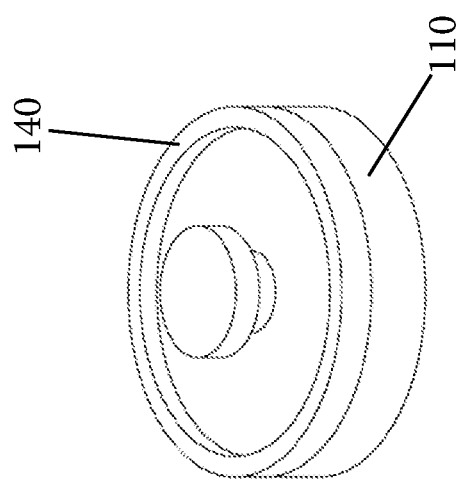
Figure 8C:
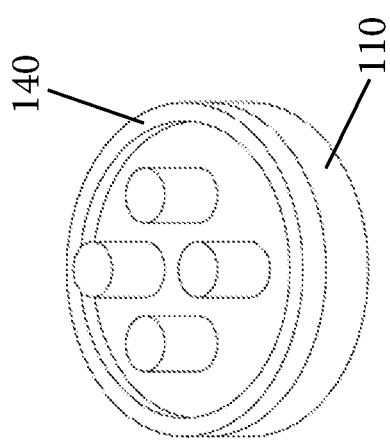

In some embodiments, the layer adjacent to the solid porous base, i.e., interface layer, is composed of a higher concentration of non-degradable polymer than the layer away from the solid porous base, i.e., load bearing layer Reference is made to FIGS. 8A-8C which show layered solid hydrogels of the present invention. The solid hydrogel layer (interface layer) 140, adjacent to the solid porous base is composed of a polymer ranging in concentration from about 20% to about 40% with 35% being preferred. The solid hydrogel layer (load bearing layer) 110, away from the solid porous base, is composed of a polymer ranging in concentration from about 10% to about 30% with 20% being preferred. The tail structures shown in the solid hydrogel models of FIGS. 8A-8C fill the geometric figures of the porous rigid base. A preferred embodiment of the solid hydrogel portion of the implant made by the method of the invention is shown in FIGS. 8A-8C and is the 1-hole design. As shown in the figures, the solid hydrogel layer 140 can be formed to have any number of different shapes including one or more outwardly protruding features that permit and facilitate mating between the layer 140 and a porous rigid base 130 (See FIG. 11A).

A preferred method of obtaining the layered hydrogels of different concentrations as well as creating a gradual transition between the two zones is set forth below.

Assembly of Implant

The improved method of assembly for the multicomponent implant utilizes a novel mold of the invention as well as a novel method which results in an implant with improved interfacial strength which has a layered hydrogel with a gradual transition between the top load bearing layer to the interface layer. This method also allows for the creation of a consistent interface layer. While the particular mold disclosed herein is novel, the method of the present invention can be performed using any mold or carrier.

Figure 11A:
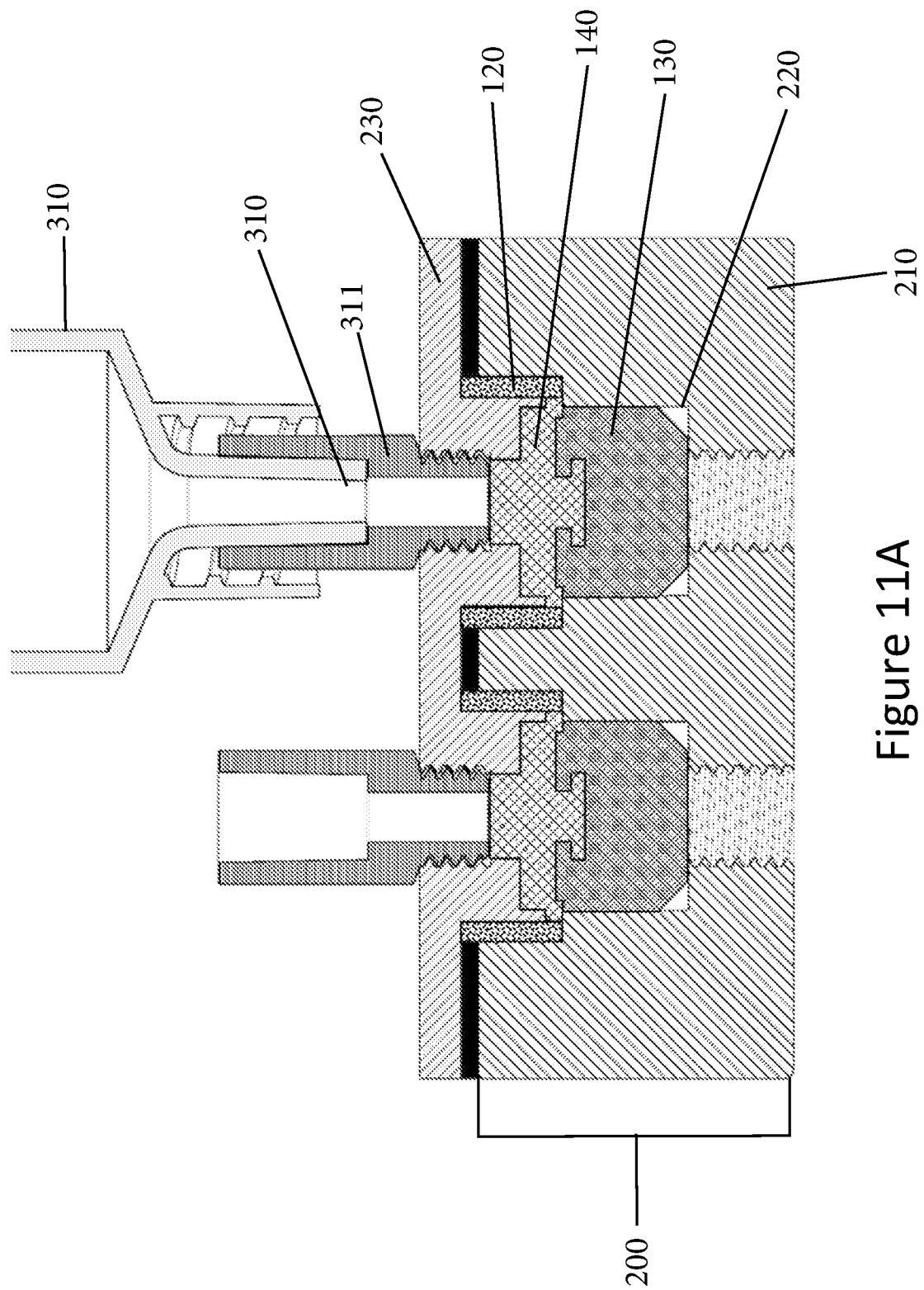
FIGS. 11A-11C illustrate one exemplary mold of the invention.

With reference to FIG. 11A, the first steps of the method of assembly comprise:
 a. placing a porous rigid base 130 into a well 220 in a base 210 of a mold 200;
 b. placing a porous hydrogel 120 in the well 220 in the base 210 of the mold 200 on top of the porous rigid base 130 and along the (side) wall of the well 220;
 c. placing a first lid 230 on the base 210 of the mold 200;
 d. introducing or injecting a first low viscosity polymer into the well 210 of the mold 200 using a tool 310 that has a nozzle or tip 311 that mates with the mold and is configured to inject material into the well 210 (FIG. 11A illustrates that the first lid 230 has openings configured to receive the nozzle 311 and position the nozzle 311 in alignment with the well 220);
 e. freezing the mold 200 with the first lid 230 containing with the porous rigid base 130 and the porous hydrogel 120 and the injected low viscosity polymer to about −20° C. for about 4 to 24 hours and subsequently thawing the base mold sponge at about 23° C. for about 4 to 12 hours resulting in formation of the solid hydrogel layer 140; and
 f. removing the first lid 230 from the base 210.

The porous rigid base 130 and porous hydrogel 120 can be obtained either commercially or by methods known in the art or as described herein. The preferred porous rigid base used in the method as described herein has a single macropore or hole. The preferred porous hydrogel used in the method is also described herein and comprises a concentration of polymer of about 10% to 40%, with a preferred concentration being about 10%.

In some embodiments, the first low viscosity polymer is poly(vinyl) alcohol or PVA but other non-biodegradable polymers can be used. Examples of other non-biodegradable polymers that can be used are polyvinyl pyrrolidone, polyacrylamide, polyethylene glycol, polyurethane, and combinations thereof.

The concentration of the first polymer is generally higher than that of the second polymer. The concentration of the first polymer ranges from about 20% to about 40% with 35% being preferred.

It is also preferred that DMSO be used as the solvent for the first polymer. Water can also be used as a solvent.

The low viscosity polymer is introduced or injected into the well 220 in the base 210 of the mold 200 that already contain the porous rigid base 130 and the porous hydrogel 120 after the first lid 230 is attached to the mold 200. The polymer can be introduced or injected by any tool 310 that is able to introduce the polymer accurately into the well of the mold. An example of such a tool is a syringe pump. As described herein, the tool 310 can have a main body that receives different nozzle tips to provide different injection characteristics, with the nozzle being selected based on the intended application and based on mold characteristics, such as well size and size of openings in the lid.

After the first polymer is injected into the mold, the entire mold is subject to freeze/thaw cycles. The preferred method involves freezing the mold at about −20° C. for about 4 to about 24 hours, with 20 hours being preferred and then thawing the construct at about 23° C. for about 4 to about 12 hours, with 4 hours being preferred. This can be varied by a person of skill in the art. Both the number of hours of freezing and/or thawing can be varied as well as the number of cycles. The preferred number of freeze/thaw cycles is about one.

After the freeze/thaw cycle of the mold, the first lid is removed and the excess polymer, e.g., PVA, can be removed.

With reference to FIG. 11A, after the first steps of the method, the resulting construct comprises a porous rigid base 130, a porous hydrogel 120 and an interface layer of a solid hydrogel 140, said interface layer comprising a concentration of polymer about 20% to 40% with 35% being preferred. As can be seen in FIG. 11A, the material that forms the solid hydrogel 140 spreads into openings/surface features of the porous rigid base 130 and therefore, when the material solidifies, the hydrogel layer 140 interfaces with (e.g., interlocks) with the porous rigid base 130.

Figure 11B:
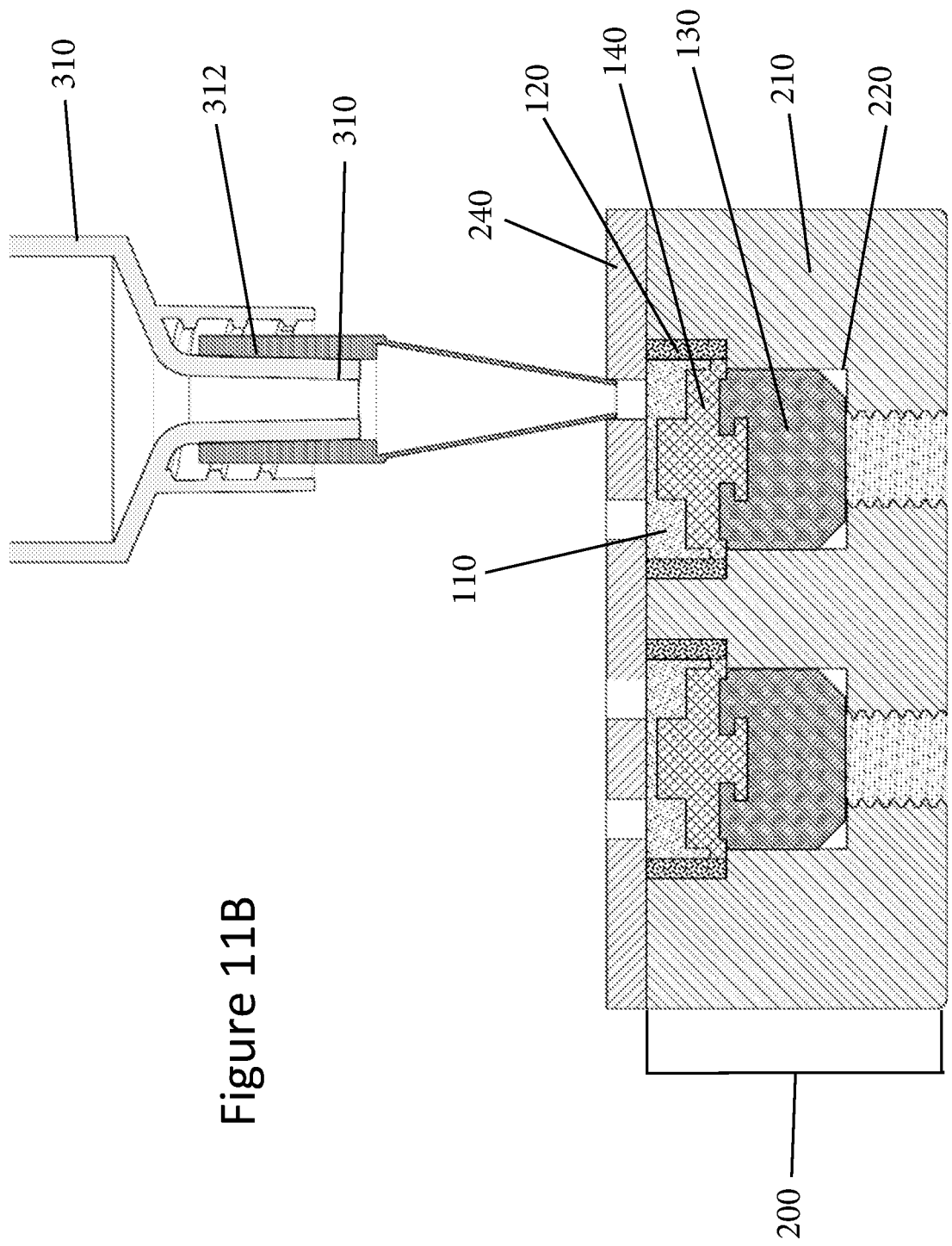

With reference to FIG. 11B, the next steps of the method of assembly comprise:
 g. placing a second lid 240 on the base 210 of the mold 200, wherein the well 220 of the mold contain a porous rigid base 130, an interface layer of a solid hydrogel 140, and a porous hydrogel 120;
 h. introducing or injecting a second low viscosity polymer into the well 220 of the mold 200 with a nozzle 312 of the tool 310 (e.g., as shown nozzle tip 312 can be of a different construction compared to nozzle tip 311 in view of the differences in opening size in the second lid 240); and
 i. freezing the mold 200 to about −20° C. for about 4 to 24 hours and subsequently thawing the mold at about 23° C. for about 4 to 12 hours resulting in the formation of the solid hydrogel layer 110; and
 j. removing the second lid 240.

In some embodiments, the second low viscosity polymer is poly(vinyl) alcohol or PVA but again other non-biodegradable polymers can be used. Examples of other non-biodegradable polymers that can be used are polyvinyl pyrrolidone, polyacrylamide, polyethylene glycol, polyurethane, and combinations thereof.

The concentration of the second polymer ranges from about 10% to about 30% with 20% being preferred.

It is also preferred that DMSO be used as the solvent for the second polymer. Water can also be used as a solvent.

The second low viscosity polymer is introduced or injected into the wells of the mold that already contain the porous rigid base 130, the interface layer of the solid hydrogel 140 and the porous hydrogel 120 after the second lid 240 is attached to the base 210 of the mold 200. The polymer can be introduced or injected by any tool 310 that is able to introduce the polymer accurately into the well of the mold. An example of such a tool is a syringe pump.

The entire mold 200 is then subject to freeze/thaw cycles. The preferred method involves freezing the mold at about −20° C. for about 4 to about 24 hours, with 20 hours being preferred and then thawing the construct at about 23° C. for about 4 to about 12 hours, with 4 hours being preferred. Again this can be varied by a person of skill in the art. Both the number of hours of freezing and/or thawing can be varied as well as the number of cycles. The preferred number of freeze/thaw cycles is one. The mold can be frozen at each interval for a time ranging from 4 to 24 hours, with 20 hours being preferred. The thaw time can range from 4 to 12 hours, with 4 hours being preferred.

After the freeze/thaw cycle of the mold, the second lid 240 is removed.

With reference to FIG. 11B, the resulting construct comprises a porous rigid base 130, a porous hydrogel 120, an interface layer of a solid hydrogel 140, said interface layer comprising a concentration of polymer about 20% to 40% with 35% being preferred, and a load bearing layer of a solid hydrogel 110, said load bearing layer comprising a concentration of polymer about 10% to 30% with 20% being preferred. As shown in FIG. 11B, the solid hydrogel 110 is formed between the porous hydrogel 120 and abuts the solid hydrogel 140.

At this point in the method of assembly, a complete multicomponent implant (joined integral structure) is made after the implant in the mold undergoes an additional about 6 to about 12 freeze/thaw cycles to allow the hydrogel to reach the desired mechanical properties. The resulting implant will have no curvature in the solid hydrogel layer. See FIG. 11B. If such a curvature is desired, further steps of the method outlined below can be performed prior to the implant undergoing the additional freeze/thaw cycles.

Figure 11C:
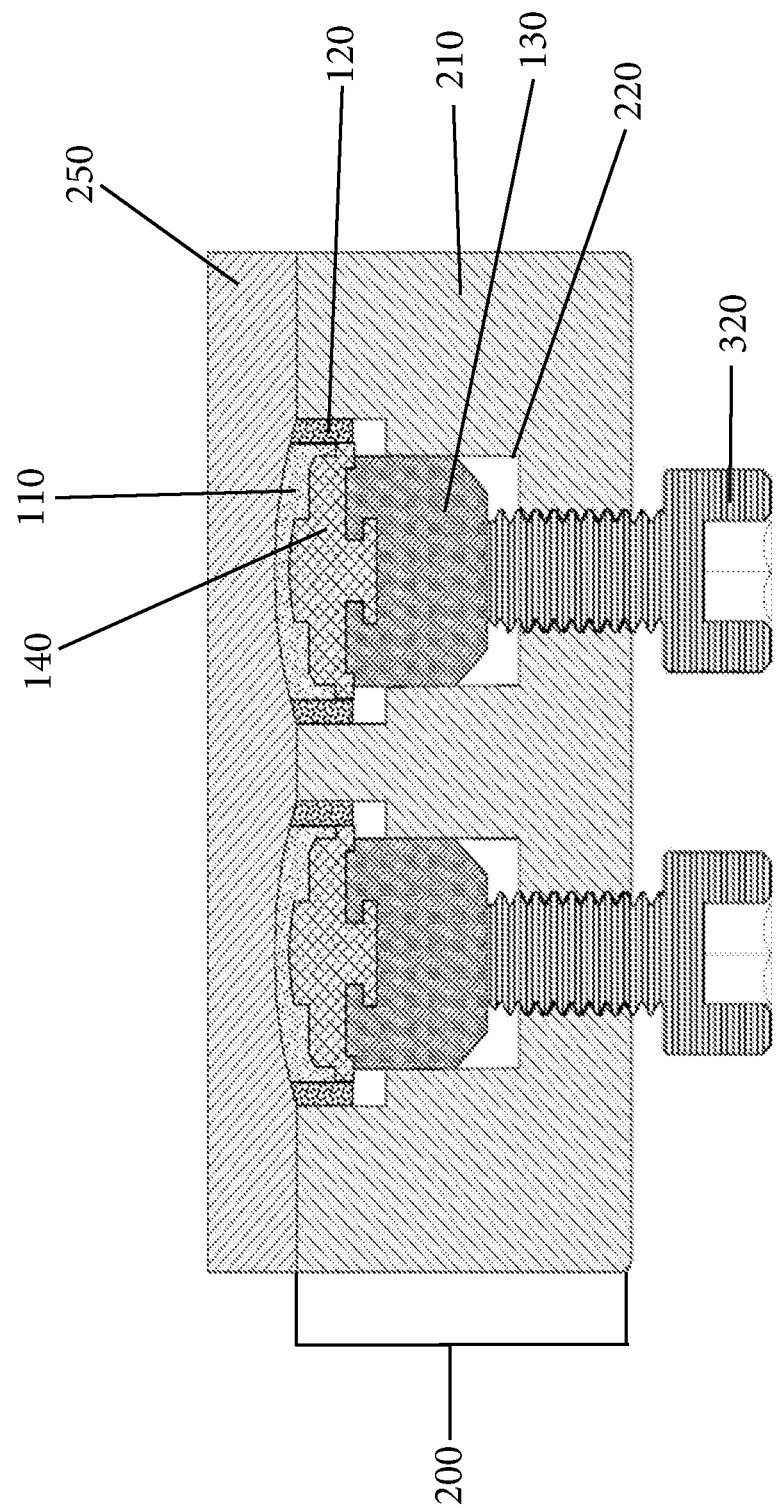

With reference to FIG. 11C, the final steps of the method of assembly can comprise:

k. placing a third lid 250 on the base 210 of the mold 200, wherein the well 220 of the mold 200 contain a porous rigid base 130, an interface layer of a solid hydrogel 140, a porous hydrogel 120, and a load bearing layer of a solid hydrogel 110, and wherein the third lid 250 has a curvature ranging from about 0 mm to about 2 mm (e.g., a bottom surface of the third lid 250 includes one or more concave-shaped recessed regions that are intended to shape the implant's surface);

l. displacing the porous rigid base 130 with a tool 320 that passes through a bottom opening formed in the mold 200 and that communicates with the well so as to displace the porous rigid base 130 a distance defined by the desired final curvature of the implant due to maintained contact with the concave-shaped recessed region of the third lid 250;

m. freezing the mold 200 with the third lid 250 containing with the porous rigid base 130, the porous hydrogel 120, an interface layer of a solid hydrogel 140, and a load bearing layer of a solid hydrogel 110 to about −20° C. for about 4 to 24 hours and subsequently thawing the base mold sponge at about 23° C. for about 4 to 12 hours;

n. removing the third lid 250, to obtain an implant comprising a porous rigid base 130, a porous hydrogel 120, an interface layer of a solid hydrogel 140, and a load bearing layer of a solid hydrogel 110; and o. removing biodegradable polymer from the porous hydrogel 120.

The third lid 250 defines the curvature of the surface of the final implant as a result of the presence of the concave recessed regions along its bottom surface. The curvature of the third interface lid can vary from no curvature at 0 mm to a maximum of 2 mm. The desired curvature of the final implant can be determined by one of skill in the art depending upon the use of and/or area in which the final implant is implanted. In other words, different third lids 250 can be offered with different degrees of curvature and the user selects the desired one.

The porous rigid base 130 can be displaced by any tool including but not limited to a screw or a peg, inserted into the bottom opening of the well 220 in the base 210 of the mold 200. The distance the implant is displaced can range from the curvature of the third lid to twice the curvature of the third lid.

As before, both the number of hours of freezing and/or thawing can be varied as well as the number of cycles. The preferred number of freeze/thaw cycles ranges from six to twelve with eight being preferred.

The biodegradable polymer, e.g., collagen sponge, can be removed from the porous hydrogel portion of the implant by any technique including but not limited to, enzymatic digestion.

It will be understood that the steps described hereinbefore can be performed in an automated manner, as by using a robotic device, pneumatic system, etc., or they can be at least partially performed as part of a manual process.

Subsequent to the assembly, the entire implant can be dehydrated prior to sterilization and implantation. Dehydration can be done by soaking the implants in 100% ethanol overnight and then allowing the ethanol to evaporate.

Supplemental agents can be added to the implant prior to insertion or implantation. Any agent that facilitates migration, integration, regeneration, proliferation, and growth of cells into and around the implant, and/or the injury or defect, and/or promotes healing of the injury or defect, and/or are chondrogenic and osteogenic, i.e., build bone and cartilage, can be added to the implant.

These agents include, but are not limited to, cytokines, chemokines, chemoattractants, anti-microbials, anti-virals, anti-inflammatories, pro-inflammatories, bone or cartilage regenerator molecules, blood, blood components, platelet rich plasma, and as combinations thereof, specific for the injury or defect being treated, repaired, and/or replaced.

Addition of these components can be performed by soaking the dehydrated hydrogel in the agent for about 15 minutes prior to implantation to allow the porous hydrogel to rehydrate with the agent.

Method of Manufacture of a Device, Construct or Material Comprising a Hydrogel or an Elastic Polymer and a Porous Rigid Material As stated above, an objective of the current invention was to develop a method of manufacture of a device, construct or material with a hydrogel-porous rigid material, e.g., PVA-metal, interface to prevent mechanical failures of the device, construct or material at the interface. The interfacial strength of any device, construct or material can be vastly improved by creating a layered hydrogel with a gradual transition between the top region layer (e.g., 20% PVA) to the interface region or layer (e.g., 35% PVA). The unique method of manufacture described herein allows for creation of a consistent interface layer (Examples 7-10).

Thus, a further embodiment of the present invention is a method of making, manufacturing and/or producing a device, construct, or material comprising a hydrogel and a porous rigid material with an interface, comprising:
a. placing a porous rigid material into a carrier;
b. introducing or injecting a first low viscosity polymer into the carrier;
c. freezing the carrier to about −20° C. for about 4 to 24 hours and subsequently thawing the carrier at about 23° C. for about 4 to 12 hours;
d. introducing or injecting a second low viscosity polymer into the carrier;
e. freezing the carrier to about −20° C. for about 4 to 24 hours and subsequently thawing the carrier at about 23° C. for about 4 to 12 hours; and
f. freezing the carrier to about −20° C. for about 4 to 24 hours and subsequently thawing the carrier at about 23° C. for about 4 to 12 hours about 6 to 12 times.

Without being bound by any theory, the method of the invention works to create this strong interface first by introducing or injecting the first low viscosity polymer in a way that it is driven into the porous rigid material, such as by a syringe or pressure system. Then because the freeze/thaw cycle is performed only once, there remains uncrosslinked hydrogel in the interface layer formed by the first low viscosity polymer. Thus, when the second low viscosity polymer is introduced or added, there is some diffusion between the two layers of differing concentrations of polymers. Again while some of the hydrogel formed by the second low viscosity polymer is crosslinked by the freeze/thaw cycle of step e., some of the hydrogel is still uncrosslinked allowing more diffusion until the final freeze/thaw cycles (step f.) that are performed from about six to twelve times and preferably eight times.

In some embodiments, the first low viscosity polymer is poly(vinyl) alcohol or PVA but other non-biodegradable polymers can be used. Examples of other non-biodegradable polymers that can be used are polyvinyl pyrrolidone, polyacrylamide, polyethylene glycol, polyurethane, and combinations thereof.

The concentration of the first polymer is generally higher than that of the second polymer. The concentration of the first polymer ranges from about 20% to about 40% with 35% being preferred.

It is also preferred that DMSO be used as the solvent for both the first and second polymers. Water can also be used as a solvent.

In some embodiments, the second low viscosity polymer is poly(vinyl) alcohol or PVA but again other non-biodegradable polymers can be used. Examples of other non-biodegradable polymers that can be used are polyvinyl pyrrolidone, polyacrylamide, polyethylene glycol, polyurethane, and combinations thereof.

The concentration of the second polymer ranges from about 10% to about 30% with 20% being preferred.

It is also preferred that DMSO be used as the solvent for both the first and second polymers. Water can also be used as a solvent.

The result of these methods of the invention is a novel device, construct, or material comprising a layered hydrogel with a gradual transition between the top region layer (e.g., 20% PVA) to the interface region or layer (e.g., 35% PVA), and a porous rigid material, with an interface that maximizes integration between the two very different layers.

Devices, constructs and materials made using this novel process have many used in the biomedical, automotive, aircraft, and aerospace fields.

Yet a further embodiment of the present invention is a method of making, manufacturing and/or producing a device, construct, or material comprising an elastic polymer and a porous rigid material with an interface, comprising:
g. placing a porous rigid material into a carrier;
h. introducing or injecting a first low viscosity polymer into the carrier, said carrier containing a chemical crosslinking agent;
i. incubating the first low viscosity polymer with the chemical crosslinking agent for a time and at a temperature to allow the chemical crosslinking agent to partially crosslink the first polymer to create an interface layer;
j. introducing or injecting a second low viscosity polymer into the carrier, said carrier containing a chemical crosslinking agent;
k. incubating the second low viscosity polymer with the chemical crosslinking agent for a time and at a temperature to allow the chemical crosslinking agent to crosslink the second polymer until the desired crosslinking percentage is reached and a layered elastic polymer is created; and
l. washing the elastic polymer to remove unreacted crosslinker and polymer.

Again without being bound by any theory, this method of the invention also works by only partially crosslinking the first low viscosity polymer such that when the second low viscosity polymer is added there is diffusion between the two layers of differing concentrations of polymers. This allows the gradual transition between the two layers of differing concentrations of elastic polymer and a stronger interface layer.

In some embodiments, the elastic polymer includes but is not limited to polyacrylamide, polyvinyl alcohol, and polyurethane.

In some embodiments, the chemical crosslinking agent is glutaraldehyde.

In some embodiments, the washing in step f. can be done with water.

Devices, constructs and materials made using this novel process have many used in the biomedical, automotive, aircraft, and aerospace fields.

The Mold

A further aspect of the current invention is the unique mold used in the method of manufacturing the implant. This mold facilitates the novel method of manufacturing. The mold can be designed to manufacture any number of implants making it ideal for scaling up the production of implants.

In one embodiment shown in FIG. 11A-11C, the mold 200 is composed of a single base 210 with at least one well 220 and three different lids 230, 240, and 250.

The base and the lids can be made using traditional manufacturing from Teflon, PEEK, PEKK, polycarbonate or ULTEM with polycarbonate being the preferred material. The mold can also be manufactured using newer technologies such as 3D printing.

The base 210 of the mold contains at least one well 220 and it is preferred that the base contain a plurality of wells up to about 50.

The size of the well(s) 220 is determined by the size of the desired final implant and can range from about 5 mm to about 20 mm in depth. The diameter of the bottom of the well where the porous rigid base 130 is placed ranges from about 5 to about 10 mm and is smaller in diameter than the top portion of the well where the porous hydrogel 120 is placed which ranges in diameter from about 10 mm to about 25 mm.

The bottom of the wells can have an opening large enough to allow a tool 320 to be inserted which is used to displace the porous rigid base after the third lid 250 is attached. The opening is determined by the size of the tool to be inserted and can range in diameter from about 3 mm to about 10 mm.

The first lid 230 is designed to fit into the base 210 in such a manner as to provide a template for the interface layer of the solid hydrogel 140 and allow for the penetration of the first low viscosity polymer that becomes the interface layer of the solid hydrogel 140. As shown in FIG. 11A, the first lid 230 is designed to have an opening that would allow a tool 310, e.g., syringe pump, to be inserted, said tool used to introduce or inject the low viscosity polymer into the well 220 in the base 210 of the mold 200, the well containing the porous rigid base 130 and porous hydrogel 120. The first lid 230 is designed such that the opening is centered over the well 220 of the base 210.

Additionally, the first lid 230 has a template which is determinative of the shape of the interface layer of the solid hydrogel 140. As can be seen in the exemplified schematic of the mold in FIG. 11A, the first lid 230 has a step design template which allows the interface layer of the solid hydrogel to form a step shape as well. It will be appreciated by those of skill in the art that the first lid 230 can be designed in any way as to obtain the desired shape of the interface layer. In one embodiment of the present invention, a mold is provided with more than one first lid 230, wherein the first lids have different templates that design the interface layer of the solid hydrogel. Examples of the different templates could include but are not limited to uncuts, dovetails and columns.

The second lid 240 is also designed to fit into the base 210 in a manner to provide a template for the load bearing layer of the solid hydrogel 110 as well as provide for the introduction or injection of the second low viscosity polymer using tool 310 into the well of the base. As shown in FIG. 11B, the second lid 230 is flat allowing the load bearing layer of the solid hydrogel to have a flattened top at this stage of production. The design also allows the two hydrogel layers to be layered and provides for a gradual transition between the two layers.

The third lid 250 is also designed to fit into the base 210. The third lid 250 is designed to define the curvature of the surface of the implant and is designed to be flat with no curvature (0 mm) up to a maximum curvature of 2 mm. It will be appreciated by one of skill in the art that the curvature of the final implant is determined by its final use and/or area of the body in which it will be implanted. In one embodiment of the invention, a mold is provided with several third lids 250 with different curvatures ranging from 0 to 2 mm and for example may include lids with curvatures of 0.2 mm 0.5 mm, 0.8 mm, 1.0 mm, 1.2 mm, 1.5 mm, 1.8 mm, and 2.0 mm. As mentioned, to impart curvature, the bottom surface of the third lid 250 includes concave shaped recessed regions.

The lids of the mold can be secured by screws around the edge of the mold and the center. Those of skill in the art will be able to determine the necessary number of screws required to prevent the lid from displacing. The porous rigid base can be displaced by a tool 320 such as a screw or clamped to an additional jig containing pins of a defined height.

Kits

The current invention also provides for kits which includes the materials needed to practice the novel method of making, manufacturing and/or producing a multicomponent implant, device, construct or material.

In one embodiment, the kit comprises the mold of the invention, including a base 210 containing at least one well 220 and at least one first lid 230, at least one second lid 240, and at least one third lid 250.

In some embodiments, the kit comprises more than one first lid, said first lids having different templates for determining the shape of the interface layer of the solid hydrogel.

In some embodiments, the kit comprises more than one third lid, said third lids having different curvatures ranging from 0 to 2 mm and for example may include lids with curvatures of 0.2 mm 0.5 mm, 0.8 mm, 1.0 mm, 1.2 mm, 1.5 mm, 1.8 mm, and 2.0 mm.

In some embodiments, a tool for introducing or injecting the first and second polymers into the well of the mold is provided for in the kit. Such a tool includes but is not limited to a syringe pump.

In some embodiments, a tool for displacing the porous rigid base when the third lid is on the base of the mold is also provided for in the kit. Such a tool includes but is not limited to a peg or screw.

In further embodiments, the kit provides starting materials for the implant including but not limited to a porous rigid base, a porous hydrogel, and low viscosity polymers at varying concentrations, ranging from about 10% to about 40%. Other materials can be included in the kit including but not limited to agents to remove biodegradable polymers, agents to dehydrate the final implant, solvents, and supplemental agents.

In some embodiments, instructions are included in the kit. Such instruction can include information regarding the assembly of the mold with the various components, tools and lids, and parameters for freezing and thawing including time, temperature and number of cycles.

EXAMPLES

The present invention may be better understood by reference to the following non-limiting examples, which are presented in order to more fully illustrate the preferred embodiments of the invention. They should in no way be construed to limit the broad scope of the invention.

Example 1—Materials and Methods for Developing and Testing an Improved Manufacture of the Hydrogel Portion of the Implant (Examples 2-4)

All handling and fabrication techniques were performed aseptically to minimize contamination with bacteria and other infectious agents.

In order to obtain a method for the improvement of the properties of the PVA hydrogels, the following variables were tested: (i) temperature, (ii) polymer blends, and (iii) changing the solvent which the PVA monomer was dissolved.

Method of Manufacture—Identical for all groups: solutions of PVA were created using an overhead stirrer in a mineral oil bath to help maintain uniform solution temperatures. Solutions were stirred until all PVA was in solution (1 to 4 hours). PVA solutions in water were heated to 90° C. and those made in DMSO were heated to 120° C. The PVA solutions were placed in a mold and then subjected to freeze/thaw cycles consisting of a 20 hour freeze cycle at −20° C. and a 4 hour thaw cycle at 23° C. in a custom-built temperature chamber.

Method of Mechanical Evaluation—Identical for all groups: eight 10 mm cylindrical plugs were cored from sheets of the hydrogel for each condition. The initial diameter of the cylindrical PVA sample was measured using electronic calipers prior to testing. The sample was then placed in the center of the lower platen of a compression testing device. The upper platen of the device was lowered until a small compressive load was read (<0.01 N) indicating that the platen had come in contact with the sample. The lower platen height was subtracted from the contact height to calculate the sample height. PVA samples were uniaxially compressed under displacement control to 30% strain at a rate of 0.5% strain using an EnduraTEC ELF 3200 load frame (TA Instruments, New Castle, Del.). Actuator load and displacement data were collected on a computer using WinTest software (TA Instruments, New Castle, Del.).

Example 2—Determination of the Best Polymer Blends

First, altering the polymer blends and the temperature at which the PVA hydrogels were dried was tested.

Polyvinyl pyrrolidone (PVP) was chosen as the secondary polymer as it has previously been used to improve the stability of PVA hydrogels (Maher, et al. 2007). For these tests, the total weight/volume (w/v) of polymer to liquid to 20% was maintained and altered the percentages (w/v) of PVP from 0 to 5%. The polymer solutions were dissolved in water and subjected to 6 freeze/thaw cycles. After the completion of the freeze/thaw cycles, the hydrogels were then washed in 100% ethyl alcohol (EtOH) for 24 hours changing the EtOH solution twice. The hydrogels were removed from the solution and dried at either room temperature (23° C.) or 85° C. for 24 hours. The hydrogels were then rehydrated 24 hours prior to performing mechanical testing performed as described in Example 1.

Figure 2:
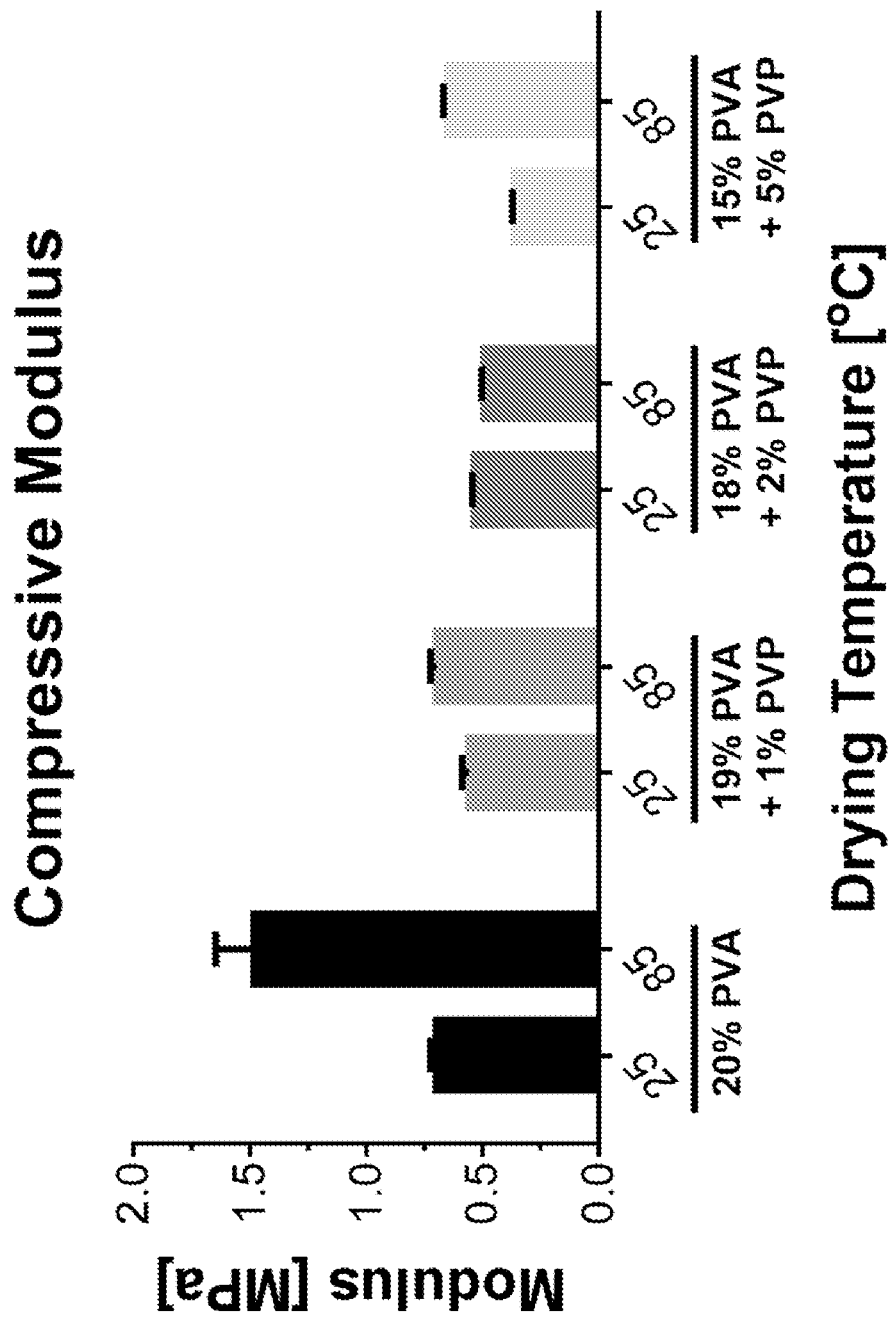
FIG. 2 is a graph of the compressive modulus of 20% PVA-PVP hydrogels reconstituted after drying at different temperatures. Different percentages of polymer solutions of PVA and PVP were mixed to create 20% (w/v) hydrogels.

The results from the mechanical testing showed that the 20% PVA dried at 85° C. had significantly improved compressive modulus (1.48±0.4 MPa) compared to the remaining conditions (FIG. 2).

Example 3—Determination of the Best Solvents

Two solvents were chosen to test: 1) double distilled $H_2O$ (ddH2O) and 2) dimethyl sulfoxide (DMSO). The solvents were used to create solutions of PVA at concentrations of 25%, 30%, and 35% PVA (w/v). The 35% PVA solutions using ddH2O as a solvent were not able to be made due to the high viscosity of the solution and therefore did not include this group in the results of this study. The solutions were then poured into 100 mm cell culture dishes and underwent 6 freeze/thaw cycles.

Figure 3:
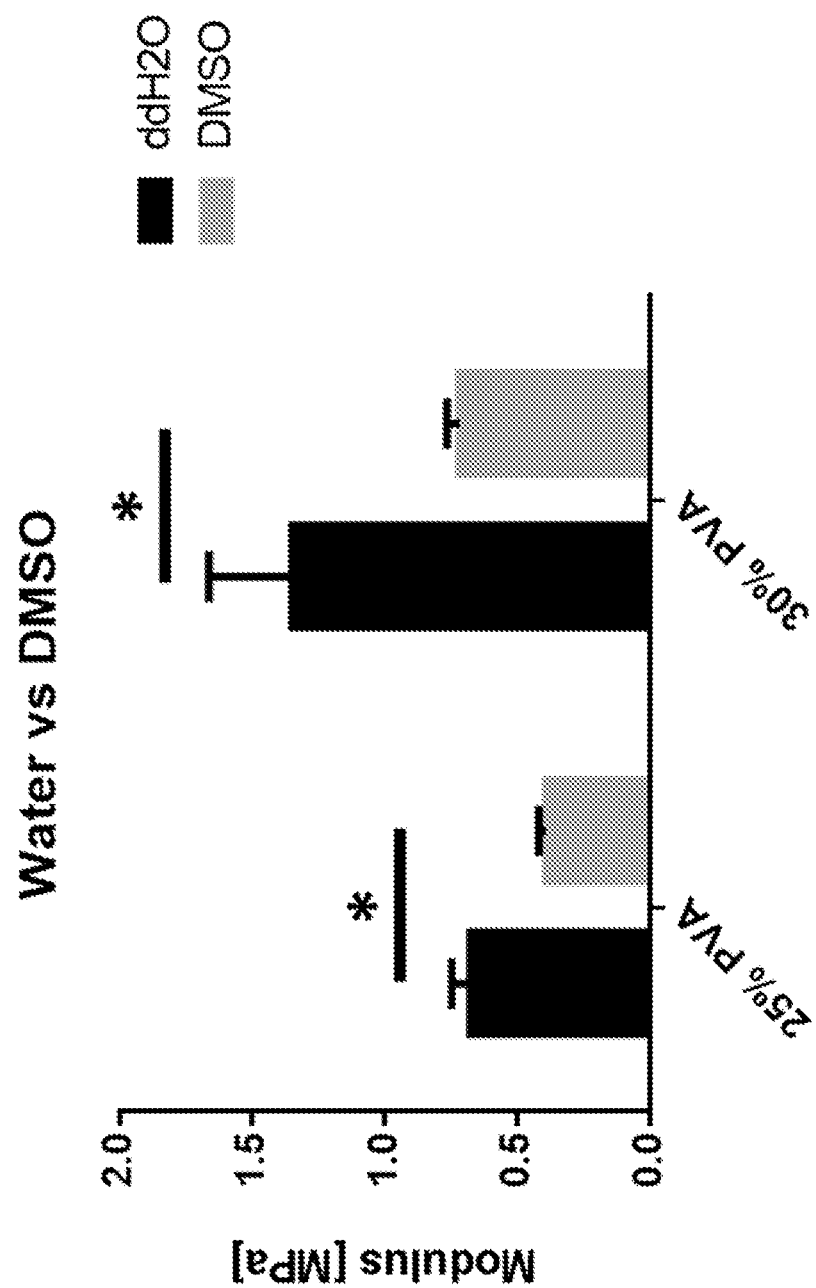
FIG. 3 is a graph comparing the compressive modulus of PVA hydrogels of differing concentrations made with either ddH2O (black bars) or DMSO (gray bars) as solvents.

The compressive moduli for PVA hydrogels (tested as described in Example 1) in ddH2O were 0.68±0.07 and 1.35±0.31 MPa for the 25% and 30% PVA groups respectively (FIG. 3). The compressive moduli for the PVA hydrogels in DMSO were 0.39±0.03 and 0.72±0.05 MPa for the 25% and 30% PVA groups, respectively. The modulus for both the 25% and 30% PVA in ddH2O groups were approximately 40% higher compared the corresponding DMSO groups.

While these data suggested that ddH2O created stronger gels, the results were based on the optimal freeze/thaw cycles for PVA dissolved in ddH2O. Therefore, tests were performed to understand how freeze/thaw cycle number altered the mechanical properties of hydrogels created from solutions of PVA in DMSO. PVA concentrations of 25% and 35% were created in DMSO and underwent either 6, 8, or 11 freeze/thaw cycles. After thawing, 10 mm cylindrical plugs were cored from the PVA sheets and washed for 3 days to remove the remaining DMSO. The compressive properties of the hydrogels were then tested.

Figure 4B:
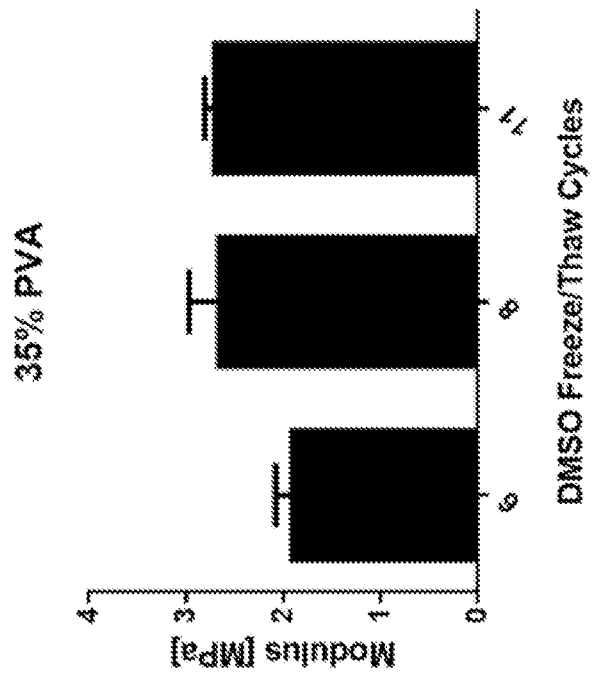
FIGS. 4A and 4B are graphs comparing the compressive modulus with increased numbers of freeze/thaw cycles (6, 8, or 11) for 25% PVA (shown in FIG. 4A) and 35% PVA (shown in FIG. 4B) with DMSO as a solvent.
Figure 4A:
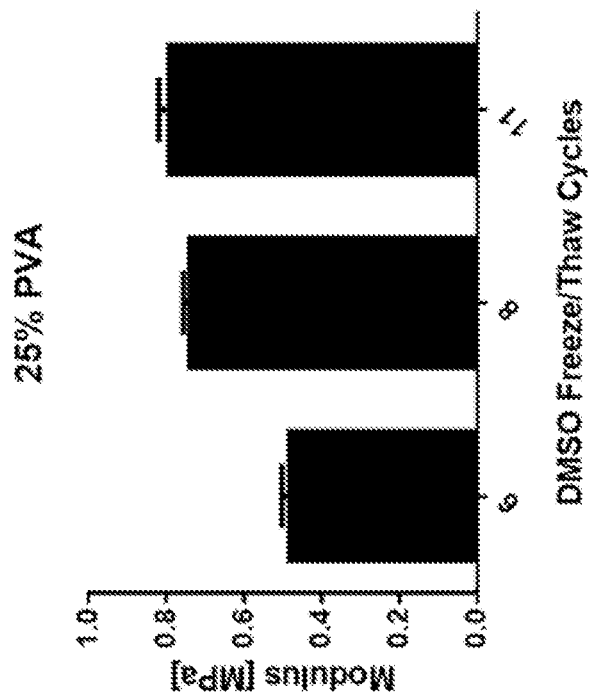

For solutions of 25% PVA (FIG. 4A), the modulus of the PVA was in the same range as the 25% PVA solutions in ddH2O after 8-11 freeze/thaw cycles. The moduli of the 25% PVA hydrogels were 0.74±0.04 MPa for 8 days of freeze/thaw and 0.79±0.06 MPa after 11 days. An increase in compressive modulus was also observed for the 35% PVA solutions (FIG. 4B) from 6 days (1.91±0.17 MPa) to 8 days (2.66±0.14) with little change from 8 days to 11 days (2.71±0.10). Based on this test, the number of freeze/thaw cycles for PVA in DMSO was increased to 8 to maintain the same properties as the hydrogels made using ddH2O.

Figure 5:
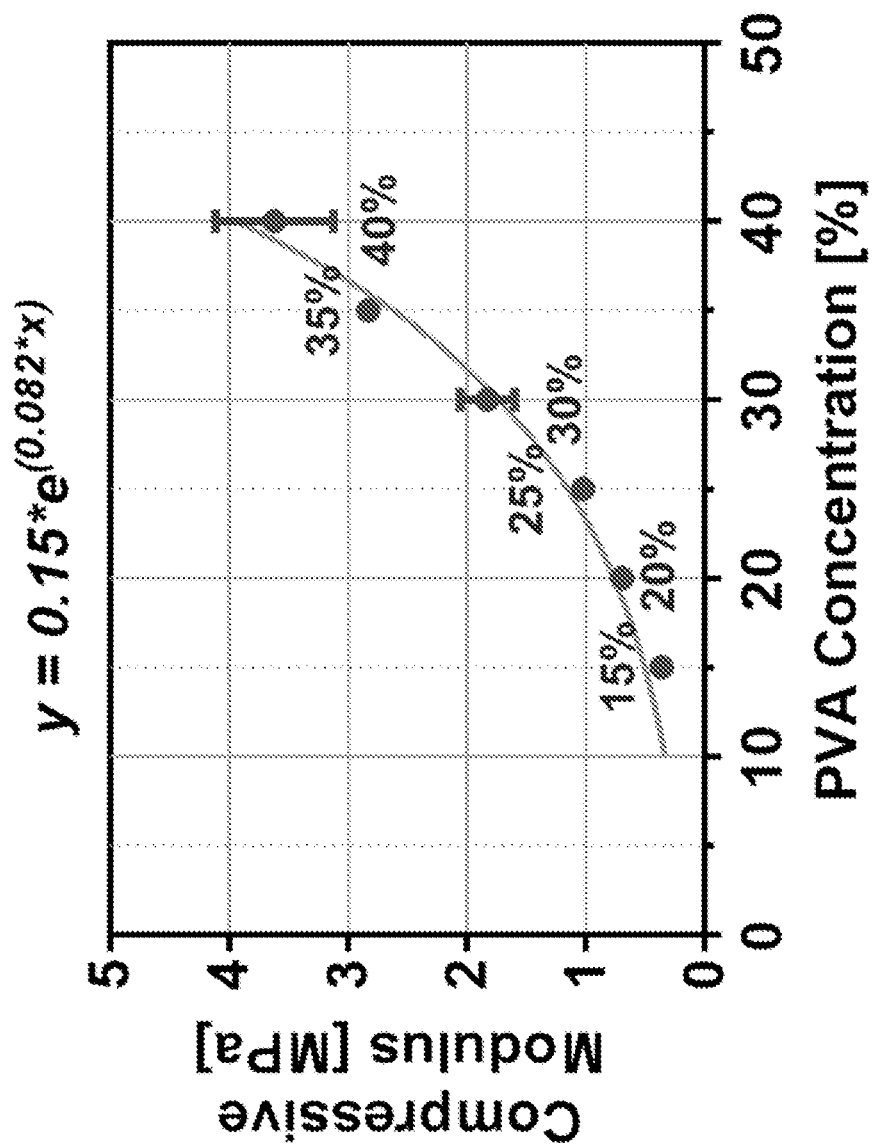
FIG. 5 is an exponential curve of the changes in compressive modulus with increasing percentages (w/v) of PVA in DMSO.

Using DMSO as a solvent, the compressive properties of the hydrogels ranging from 15% to 40% (w/v) PVA were measured (FIG. 5). The hydrogels fit an exponential curve with maximum properties at 40% PVA of 3.62±0.5 MPa. While the 40% hydrogels had superior mechanical properties, the solution was difficult to manipulate due to its increased viscosity and were not used in future tests.

Example 4—Layered Hydrogels

The feasibility of creating layered hydrogels was tested. Samples were sent to the laboratory of Dr. Markus Wimmer at Rush University (Chicago, Ill.) for microindentation testing. A 50 um round ended indenter was used to perform two rounds of 30 indentations, 5 nm in depth, along the length of each hydrogel tested. For layered hydrogels consisting of 20% and 35% PVA, indentations were made perpendicular to the interface between the two PVA concentrations.

Microindentation tests were first optimized on uniform PVA hydrogels of 25% and 30% concentration that were previously tested. The properties were consistent across the hydrogels, with the 25% PVA having measured properties of 0.17±0.012 MPa and the 30% PVA having properties of 0.25±0.042 MPa.

Figure 6:
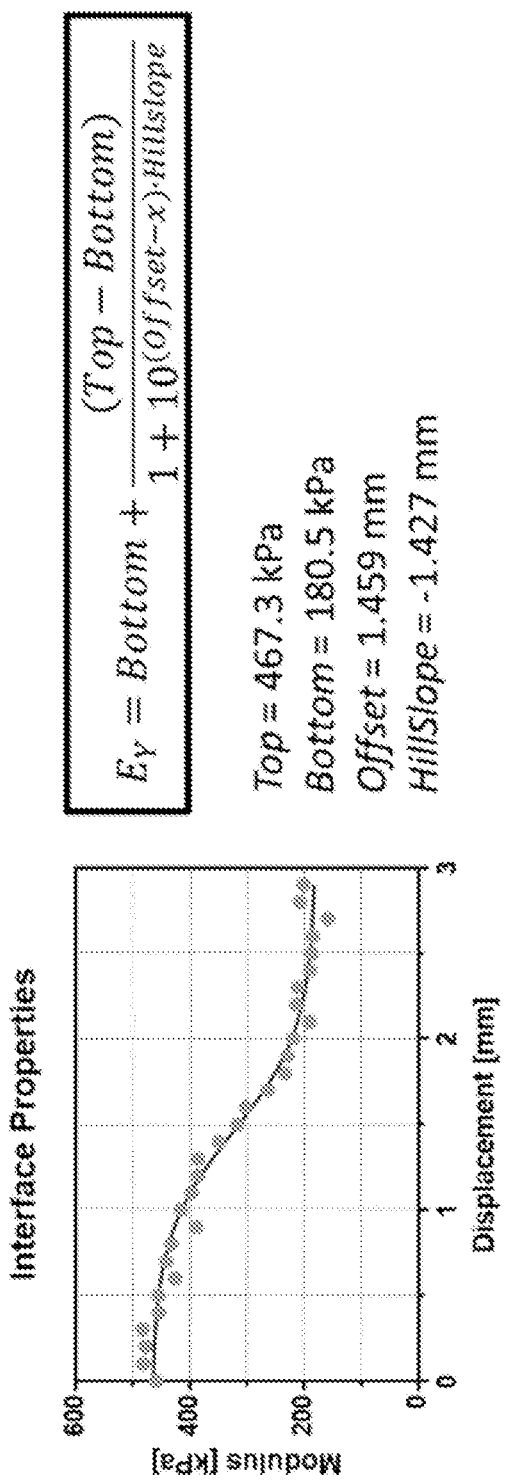
FIG. 6 is a graph of the results of the indentation test on the layered hydrogel. The graph shows the indentation results across the interface between the two PVA concentrations (35% and 20%) (dots) and the sigmodal fit (line).

Tests were then performed on two layered hydrogels that consist of a 20% and 35% PVA layer. The properties of the hydrogels fit a sigmodial curve and had a gradual transition from the 35% to 20% PVA layers (FIG. 6). From the sigmodial fit, the 35% PVA has a modulus of 0.48 MPa and the 20% has a modulus of 0.18 MPa with a transition zone that spanned 1.4 mm of the hydrogel.

The results set forth in Examples 2-4 showed that higher concentration PVA hydrogels can be created using DMSO as the solvent while maintaining the same mechanical properties. Hydrogels of different concentrations could be layered and created a gradual transition between the two zones. The resulting hydrogel composition was used to design the implants tested in Example 5. See FIGS. 8A-8C.

Figure 7:
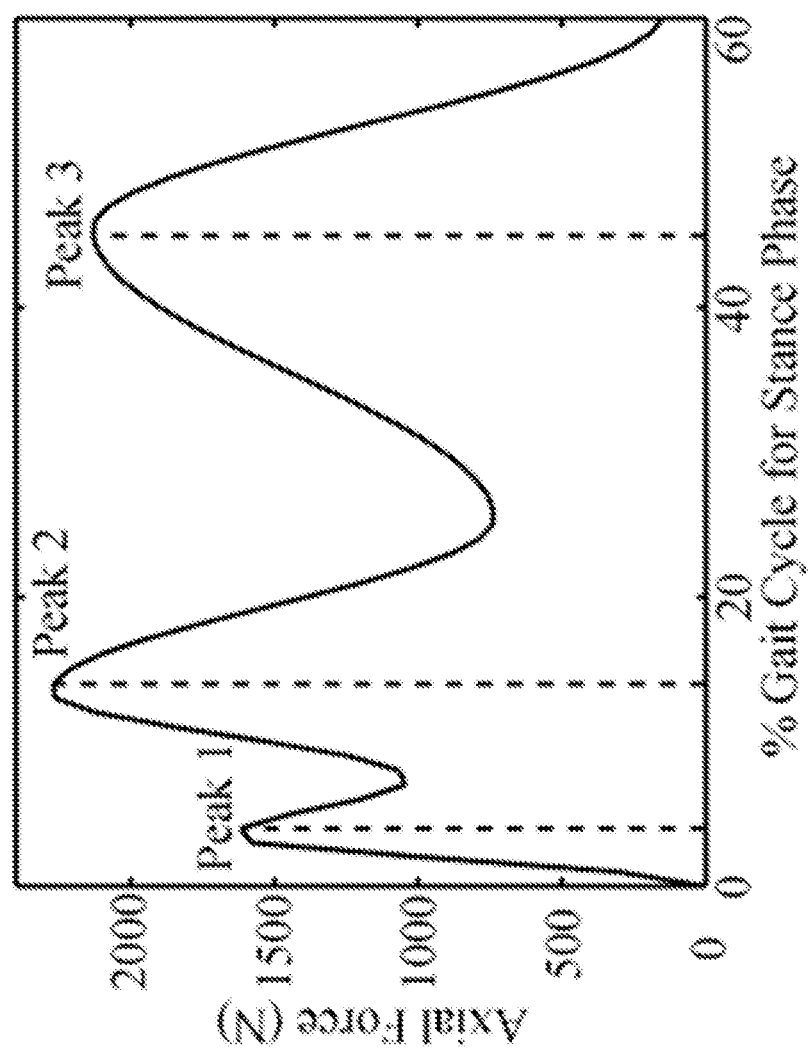
FIG. 7 is a graph of the three peak stress locations (dotted line) at which shear stresses were analyzed in Example 5.

Example 5—Testing Various Implant Designs Using Computational Finite Element (FE) Models A previously developed and validated FE model of a human knee joint (Guo et al., 2015) was used to assess the mechanical performance of the implant designs. In brief, a subject-specific model of a human cadaveric knee was created based on magnetic resonance images (MRI). Knee-specific kinematics measured from cadaveric simulations of gait were combined with axial force inputs which were then applied to the mid-point of the femoral epicondylar axis. Articular cartilage and menisci were modeled as elastic materials. The menisci were assumed to be transversely isotropic. Material properties were set as the mid-values of previously reported measurements. Meniscal attachments were modeled as linear springs. Bones and the implant base were assumed to be rigid and were represented by rigid boundary condition. All surface-to-surface contacts in the model were assumed to be frictionless. All implants of different designs were placed in the same location on the medial femoral cartilage, and the surfaces of the implants were assumed to match cartilage's curvature. The FE model was run through a gait cycle and results of shear stress at the implant-bone interface at the three local peaks of axial force (i.e., 4%, 14%, and 45% of gait cycle) were output (FIG. 7).

The FE model was used to understand the forces at the PVA-metal interface for 3 different metal base designs: 4-hole; 1-hole; and dovetail (FIGS. 8A-8C). Analysis of the principal stress directions was performed and indicated that the major stresses were in compression and shear. Therefore, the analysis focused on shear.

For all three designs, shear stress at the implant-bone interface at 45% of the gait cycle was the highest at the three timepoints of the gait cycle studied, and shear stress at 4% of the gait cycle was the smallest. In 45% of the gait cycle, peak shear stresses at the implant-bone interface were around 3 MPa for the 4-hole and dovetail designs, while it was 2.3 MPa for the 1-hole design. At 4% of the gait cycle, peak shear stress at the implant-bone interface were about 0.8 MPa for the 1-hole and dovetail designs, while it was 1.7 MPa for the 4-hole design. Shear stress concentration was found at the flat interface of the 4-hole design, while shear stress concentration was found at the root of the tail structures for the 1-hole and dovetail designs. The cylinders of the 4-hole design had higher shear stress than the tail structures of the 1-hole and dovetail designs, and most parts of the tail structures of the 1-hole and dovetail designs had shear stress close to 0 MPa, which indicates that the hydrogel in the macroporous features are protected from shear stresses.

Example 6—Manufacture of the Porous Rigid Base Portion of the Implant

A titanium (Ti6Al4V or Ti6Al4VELI) cylinder with a diameter of 9 mm and pores of about 150 to 500 μm in size and a 45° taper at the bottom, was 3D printed with one additional hole (1.3 mm diameter and 4.5 mm deep) at the top surface of the base. A 0.5 mm step was also created. These bases were designed using computer aided design and created using techniques such as electron beam melting or by laser metal sintering.

Example 7—Assembly of the Implant

A collagen sponge was impregnated with 10% PVA in DMSO. After a single freeze/thaw cycle, concentric punches were used to core the sponge to form the porous hydrogel edge.

The porous metal bases made of titanium (Ti) or PEEK were placed into the base mold (See, FIGS. 11A-11C) after which the porous hydrogel was placed in the well of the base mold, along the edge, on top of the metal base.

The first lid was placed on the base mold and liquid 35% PVA in DMSO was injected through the injection port into the wells of the base mold using a syringe pump. The entire mold was then placed into the temperature control system to undergo a single freeze/thaw cycle. The lid was removed and excess PVA was cut with scissors.

The second lid was then secured to the base mold. Liquid 20% PVA in DMSO was then injected through the injection port of the wells in the mold and the entire mold was then placed into the temperature control system to undergo a single freeze/thaw cycle. The second lid was removed.

The third lid was then secured to the base mold. The third lid was secured to the base mold. The third lid had a curvature of 1 mm.

A screw was inserted into the bottom of the well and the metal base was displaced 1 mm by turning the screw. The entire mold was then placed into the temperature control system to undergo eight freeze/thaw cycles.

The collagen sponge was digested away using collagenase and the implant was rinsed for 1 week in ddH2O, changing solution every day, to remove residual enzyme and DMSO. The implant was then placed in 100% EtOH overnight. The ethanol was then allowed to evaporate leaving the final dehydrated implant.

Example 8—Shear Testing of the Implants Made by the Improved Method of Manufacture Before shear testing, the implants made using the method of Example 7 were soaked for 15 minutes and then implanted in a 9 mm hole predrilled into a block of wood to simulate the surgical procedure, ensuring that the results from shear testing would recapitulate the post-implantation interface stability. The implants are then removed for the wood and soaked in water for 24 hours to allow the implants to fully rehydrate.

The initial diameter of the cylindrical PVA portion of the sample was measured twice (in perpendicular directions) using electronic calipers prior to testing. The titanium (Ti) or PEEK base of the sample was secured in the mobile fixture of the testing device while the PVA portion of the sample was inserted into the stationary fixture of the testing device. A screw was used to position the sample such that the PVA-Ti/PEEK interface was located in the gap between the mobile and stationary fixtures. The screw also prevented the hydrogel from torqueing the fixture, ensuring that a pure translational force was applied at the interface. The mobile fixture containing the Ti/PEEK base was then moved uniaxially upward at a rate of 0.03 mm/s under displacement control to apply shear to the PVA-Ti/PEEK interface using an EnduraTEC ELF 3200 load frame (TA Instruments, New Castle, Del.).

Testing was performed until a drop in load was witnessed indicating that interfacial failure had occurred. Actuator load and displacement data were collected on a computer using WinTest software (TA Instruments, New Castle, Del.). The interfacial shear stress was calculated using the maximum force and displacement as previously described in Woodfield (2000). The safety factor for each design was calculated by dividing the maximum interfacial stress, as computed in the FE model, by the failure stress as measured experimentally.

Figures 9A, 9B:
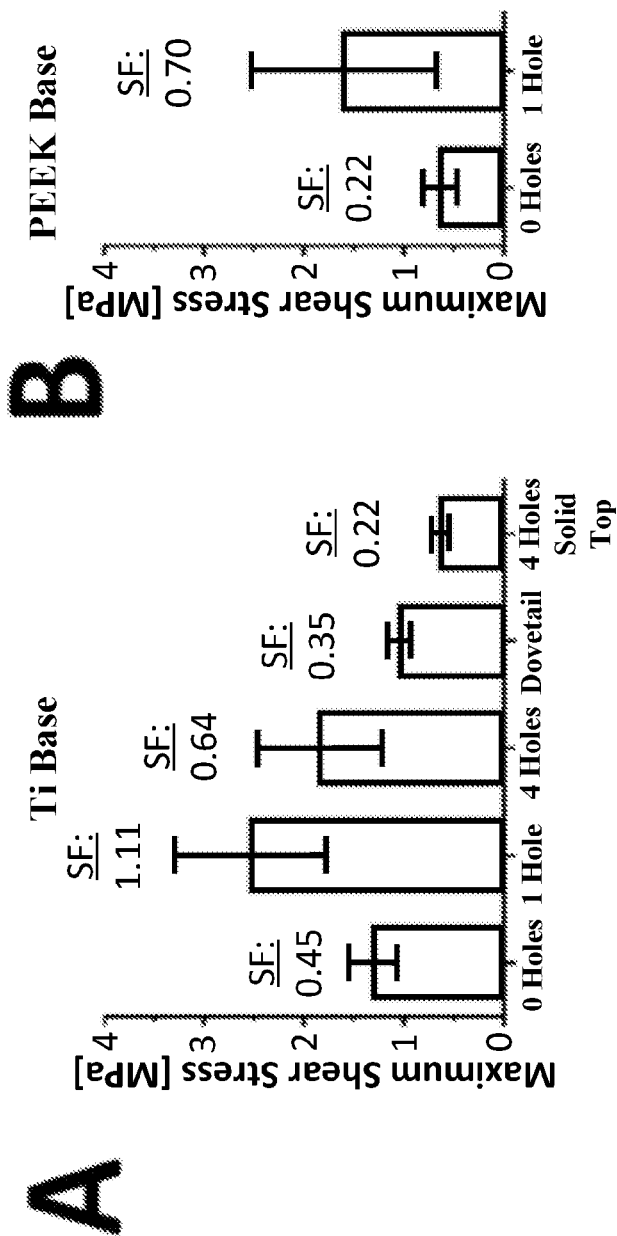
FIGS. 9A-9B are graphs of the maximum shear stress at failure for the Ti base (FIG. 9A) and the PEEK base (FIG. 9B).
Figure 10:
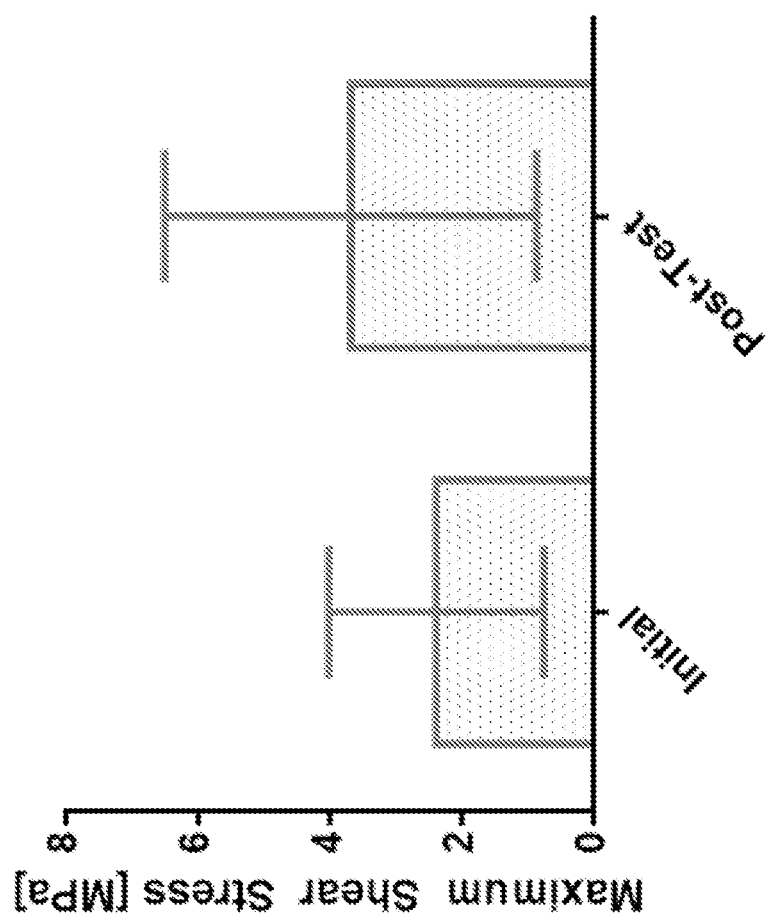
FIG. 10 is a graph of the maximum shear stress at failure after wear testing of the one-hole design. The initial testing bar is the shear test results from Example 5 for the 1-hole design.

The rehydrated implants were tested to failure and the safety factors calculated for implants made from Ti (FIG. 9A) and PEEK (FIG. 9B) bases. After a drop in properties was noted in the software the implants were removed and failure area was noted. For all 1-hole Ti implants, no implant was noted to fail past the macroporous feature.

The porous titanium base with a single macroporous hole was identified as the optimal combination to create a safety of factor of greater than 1.

Example 9—Fatigue Testing of the Implants Made by the Improved Method of Manufacture While FE models can be used to analyze the ability of a device to withstand physiological shear and tensile stresses throughout a single gait cycle, experimental models can directly assess the response of the interface to repetitive loading. Thus, devices made by the method of Example 7 were subjected to 200,000 cycles of combined axial and shear forces to simulate walking.

The femoral condyles from mature cadaveric equine knee joints were removed. Four 9 mm cylindrical defects in the central region of the femoral block were cored perpendicular to the cartilage surface using the instruments designed for in vivo implantation of the device. The resultant osteochondral defects measured 9 mm diameter×10 mm deep. The 1-hole device designs which had the highest safety factor identified in Example 8 (n=10/design) were implanted, and allowed to rehydrate in PBS overnight at 37° C. The femoral block with implanted devices were secured into the specimen clamp of a custom-built rolling and sliding machine. A ⅜ inch hole was drilled into the other femoral condyle and a ½ inch stainless steel rod was tamped through the hole to create the rotation axis. The condyle with rod was then secured to the rotation axis of the machine. The maximum axial force, as determined across all FE models, equated to 23 pounds of weight. To ensure that the implants could withstand higher loads, 50 pounds of weight was applied to the top of the machine which equated to a compressive stress of 20 MPa. The femoral block translated at a rate of 10 cm/sec across the full 10 cm span for 200,000 cycles to simulate the rate of anterior-posterior translation during normal walking (Gilbert, et al. 2015) for a three-month period.

The implants that were tested for 200,000 cycles at twice the physiologic load showed no "failure" defined as: 1) the PVA layer dislocates before reaching 200,000 cycles; or 2) the failure stress at the completion of testing is below 75% of that prior to testing. There was no dislocation of the PVA layer.

Example 10—Mechanical Testing

At the end of fatigue testing in Example 9, the implants were removed from the femoral condyles and shear testing was performed as previously described in Example 5.

Results from the shear test shown in FIG. 12, found no differences between the initial and post-wear tested implants, suggesting that even after repetitive, worse-case scenario loading conditions, the implant maintained structural integrity.

These results also showed no sign of failure of the implants as the failure stress at the completion of testing was not 75% of the stress prior to testing.

REFERENCES

1. Bekkers et al., (2009). "Treatment selection in articular cartilage lesions of the knee: a systematic review." *Am. J. Sports Med.* 37 Suppl 1: 148S-155S.
2. Choi et al., (1990) "The elastic moduli of human subchondral, trabecular, and cortical bone tissue and the size-dependency of cortical bone modulus." *Journal of Biomechamics* 23(11):1103-13.
3. Cole and Lee, (2003) "Complex knee reconstruction: articular cartilage treatment options." *Arthroscopy* 19 Suppl 1: 1-10.
4. Deneweth et al., (2013) "Heterogeneity of tibial plateau cartilage in response to a physiological compressive strain rate." *J. Orthop. Res.* 31(3):370-5.
5. Gilbert et al., (2013) "Dynamic contact mechanics on the tibial plateau of the human knee during activities of daily living." *Journal of Biomechanics* 47(9):2006-12.
6. Guo et al., (2015) "A statistically-augmented computational platform for evaluating meniscal function." *Journal of Biomechanics* 48(8):1444-53.
7. Magnussen et al., (2008) "Treatment of focal articular cartilage defects in the knee: a systematic review." *Clin. Orthop. Relat. Res.* 466(4): 952-962.
8. Maher et al., (2007) "Nondegradable hydrogels for the treatment of focal cartilage defects." *Journal of Biomedical Materials Research Part A* 83(1):145-55.
9. Mauck et al. (2002). "Influence of seeding density and dynamic deformational loading on the developing structure/function relationships of chondrocyte-seeded agarose hydrogels." *Ann. Biomed. Eng.* 30(8):1046-1056.
10. Radin et al., (1970) "A comparison of the dynamic force transmitting properties of subchondral bone and articular cartilage." *J. Bone Joint Surg. Am.* 52(3):444-56.
11. Shelbourne et al., (2003). "Outcome of untreated traumatic articular cartilage defects of the knee: a natural history study." *J. Bone Joint Surg. Am.* 85-A Suppl 2:8-16.
12. Woodfield, (2000) "Interfacial Shear Strength Criteria for Tissue-Engineered Cartilage Anchored To Porous Synthetic Scaffolds" Masters Thesis, University of Toronto.

The invention claimed is:

1. A method of making, manufacturing and/or producing an implant suitable for implantation into a mammal for the treatment, repair or replacement of defects or injury in biological tissue, comprising the steps of:
   a. placing a porous rigid base into a well in a mold;
   b. placing a porous hydrogel in the well on top of the porous rigid base;
   c. placing a first lid on the mold;
   d. introducing or injecting a first polymer into the well of the mold;
   e. freezing the mold to about −20° C. for about 4 to 24 hours and subsequently thawing the mold at about 23° C. for about 4 to 12 hours;
   f. removing the first lid;
   g. placing a second lid on the mold;
   h. introducing or injecting a second polymer into the well of mold; and
   i. freezing the mold to about −20° C. for about 4 to 24 hours and subsequently thawing the mold at about 23° C. for about 4 to 12 hours.

2. The method of claim 1, wherein the first polymer is chosen from a group consisting of poly(vinyl) alcohol, polyvinyl pyrrolidone, polyacrylamide, polyethylene glycol, polyurethane, and combinations thereof.

3. The method of claim 2, wherein the first polymer is poly(vinyl) alcohol at a concentration of about 20% to about 40%.

4. The method of claim 1, wherein the second polymer is poly(vinyl) alcohol, polyvinyl pyrrolidone, polyacrylamide, polyethylene glycol, polyurethane, and combinations thereof.

5. The method of claim 4, wherein the second polymer is poly(vinyl) alcohol at a concentration of about 10% to about 30%.

6. The method of claim 1, wherein the first and second polymer are in dimethyl sulfoxide.

7. The method of claim 1, wherein the first and second polymer are injected into the mold using a syringe pump.

8. The method of claim 1, wherein step i. is performed about six to about twelve times.

9. The method of claim 1, further comprising the step of removing degradable polymer in the implant.

10. The method of claim 1, further comprising the step of dehydrating the implant prior to implantation.

11. The method of claim 1, further comprising the steps of:
   j. placing a third lid on the mold, wherein the third lid has a curvature ranging from about 0 mm to about 2 mm;
   k. displacing the porous rigid base with a tool which displaces the porous rigid base a distance defined by the desired final curvature of the implant; and
   l. freezing the mold to about −20° C. for about 4 to 24 hours and subsequently thawing the mold at about 23° C. for about 4 to 12 hours.

12. The method of claim 1, wherein porous rigid base comprises geometric features.

\* \* \* \* \*